(12) United States Patent
Okuda et al.

(10) Patent No.: US 11,093,787 B2
(45) Date of Patent: Aug. 17, 2021

(54) METHODS, APPARATUSES, AND SYSTEMS FOR CREATING 3-DIMENSIONAL REPRESENTATIONS EXHIBITING GEOMETRIC AND SURFACE CHARACTERISTICS OF BRAIN LESIONS

(71) Applicant: THE BOARD OF REGENTS OF THE UNIVERSITY OF TEXAS SYSTEM, Austin, TX (US)

(72) Inventors: Darin T Okuda, Coppell, TX (US); Braeden D Newton, Fort Mcmurray (CA)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 51 days.

(21) Appl. No.: 16/312,983

(22) PCT Filed: Jun. 30, 2017

(86) PCT No.: PCT/US2017/040229
§ 371 (c)(1),
(2) Date: Dec. 21, 2018

(87) PCT Pub. No.: WO2018/005939
PCT Pub. Date: Jan. 4, 2018

(65) Prior Publication Data
US 2019/0197347 A1    Jun. 27, 2019

Related U.S. Application Data

(60) Provisional application No. 62/357,477, filed on Jul. 1, 2016.

(51) Int. Cl.
*G06K 9/62* (2006.01)
*G06K 9/34* (2006.01)
(Continued)

(52) U.S. Cl.
CPC ............. *G06K 9/6201* (2013.01); *G06K 9/34* (2013.01); *G06T 7/11* (2017.01); *G06T 15/08* (2013.01);
(Continued)

(58) Field of Classification Search
CPC .. G06K 9/6201; G06K 9/34; G06K 2209/051; G06K 9/342; G06K 9/0014;
(Continued)

(56) References Cited

U.S. PATENT DOCUMENTS

| 6,614,226 B2 | 9/2003 | Wedeen | |
| 2003/0096406 A1* | 5/2003 | Atala | A61L 27/18 435/366 |

(Continued)

FOREIGN PATENT DOCUMENTS

| EP | 1974313 | 10/2008 |
| EP | 2419174 | 2/2012 |

(Continued)

OTHER PUBLICATIONS

International Preliminary Report on Patentability Issued in Corresponding PCT Application No. PCT/US2017/040229, dated Jan. 1, 2019.

(Continued)

*Primary Examiner* — Nimesh Patel
(74) *Attorney, Agent, or Firm* — Norton Rose Fulbright US LLP

(57) ABSTRACT

Methods, apparatuses, systems, and implementations for creating 3-dimensional (3D) representations exhibiting geometric and surface characteristics of brain lesions are disclosed. 2D and/or 3D MRI images of the brain may be acquired. Brain lesions and other abnormalities may be identified and isolated with each lesion serving as a region of interest (ROI). Saved ROI may be converted into stereo- (Continued)

lithography format, maximum intensity projection (MIP) images, and/or orthographic projection images. Data corresponding to these resulting 3D brain lesion images may be used to create 3D printed models of the isolated brain lesions using 3D printing technology. Analysis of the 3D brain lesion images and the 3D printed brain lesion models may enable a more efficient and accurate way of determining brain lesion etiologies.

22 Claims, 10 Drawing Sheets

(51) Int. Cl.
*G06T 7/11* (2017.01)
*G06T 15/08* (2011.01)
*G06T 17/00* (2006.01)
*G16H 30/40* (2018.01)
*A61B 5/055* (2006.01)

(52) U.S. Cl.
CPC ............ *G06T 17/00* (2013.01); *A61B 5/055* (2013.01); *G06K 2209/051* (2013.01); *G06T 2207/10088* (2013.01); *G06T 2207/30016* (2013.01); *G06T 2207/30096* (2013.01); *G06T 2210/41* (2013.01); *G16H 30/40* (2018.01)

(58) Field of Classification Search
CPC ............ G06K 9/00369; G06K 9/6202; G06K 9/6212; G06K 9/6214; G06K 9/0061; G06K 9/2054; G06T 15/08; G06T 7/11; G06T 2210/41; G06T 2207/30016; G06T 2207/30096; G06T 7/0012; G06T 2207/10081; G06T 7/187; G06T 2207/20156; G06T 7/12; G06T 7/136; G06T 17/005; G06T 2207/30024; G06T 2207/30101; G06T 7/20; G06T 7/60; G06T 7/70; G06T 17/00; G06T 2207/10072; G06T 2207/10088; G06T 2207/10132; G06T 2207/20101; G06T 2207/20104; G06T 7/149; G16H 30/40; G16H 10/60; G16H 50/30; G16H 30/20; G16H 40/67; G16H 50/20; G16H 50/50; A61B 5/055; A61B 17/00234; A61B 17/16; A61B 2017/00867; A61B 3/0041; A61B 3/032; A61B 3/036; A61B 3/103; A61B 3/111; A61B 3/18; A61B 5/0022; A61B 18/1492; A61B 1/00009; A61B 1/00057; A61B 1/00179; A61B 1/00193; A61B 1/05; A61B 1/051; A61B 1/0623; A61B 1/0638; A61B 1/227; A61B 3/0058; A61B 3/024; A61B 3/107; A61B 5/0013; A61B 5/002; A61B 5/0075; A61B 5/0086; A61B 5/0205; A61B 5/11; A61B 5/1128; A61B 5/7221; A61B 5/7246; A61B 5/7264; A61B 5/7275; A61B 6/032; A61B 6/5247; A61B 2576/00; A61L 31/16; A61L 31/18; A61L 2300/258; A61L 2300/414; A61L 27/54; A61L 31/14; A61L 31/148; A61L 27/3804; A61L 2300/00; A61L 2430/16; C12Q 1/6809; C12Q 1/6886; C12Q 2537/165; C12Q 2600/112; C12Q 1/6869; C12Q 2600/136; G01N 33/564; G01N 33/57415; G01N 2500/04; G01N 15/0227; G06F 19/321; G06F 19/3418; G06F 3/00; G06F 3/0482; G06F 19/00; G06F 2101/04; G06F 3/017; G06F 8/34

See application file for complete search history.

(56) References Cited

U.S. PATENT DOCUMENTS

| | | | |
|---|---|---|---|
| 2004/0051527 A1* | 3/2004 | Mugler, III | G01R 33/5615 324/309 |
| 2004/0147830 A1* | 7/2004 | Parker | A61B 6/50 600/407 |
| 2004/0204644 A1 | 10/2004 | Tsougarakis et al. | |
| 2004/0267102 A1 | 12/2004 | Skladnev et al. | |
| 2006/0120608 A1 | 6/2006 | Luo et al. | |
| 2008/0260221 A1* | 10/2008 | Unal | G06T 7/149 382/128 |
| 2010/0098309 A1* | 4/2010 | Graessner | G06K 9/00 382/131 |
| 2010/0260396 A1 | 10/2010 | Brandt et al. | |
| 2010/0290689 A1* | 11/2010 | Gupta | G06T 7/0012 382/131 |
| 2013/0050208 A1* | 2/2013 | Lin | G06T 17/20 345/420 |
| 2013/0314086 A1 | 11/2013 | Li et al. | |
| 2014/0056496 A1* | 2/2014 | Kwak | G01R 33/5611 382/131 |
| 2014/0081129 A1* | 3/2014 | Lu | A61B 5/066 600/424 |
| 2014/0185888 A1 | 7/2014 | Kelm et al. | |
| 2014/0222462 A1* | 8/2014 | Shakil | G06Q 50/22 705/3 |
| 2015/0025666 A1 | 1/2015 | Olivieri et al. | |
| 2015/0213600 A1* | 7/2015 | Kyriakou | G06T 15/08 345/424 |
| 2015/0343708 A1 | 12/2015 | Gerstle et al. | |
| 2016/0303804 A1 | 10/2016 | Grbic et al. | |

FOREIGN PATENT DOCUMENTS

| | | |
|---|---|---|
| GB | 2470455 A | 11/2010 |
| GB | 2470455 B | 7/2013 |
| SG | 189313 | 5/2013 |
| WO | WO 2007/079207 A2 | 7/2007 |
| WO | WO 2007/079207 A3 | 7/2007 |
| WO | WO 2007/079207 B1 | 10/2008 |
| WO | WO 2019/079519 | 7/2010 |
| WO | WO 2010/119012 | 10/2010 |

OTHER PUBLICATIONS

International Search Report and Written Opinion Issued in Corresponding PCT Application No. PCT/US2017/040229, dated Sep. 15, 2017.
Akkad, et al., "Multiple Sclerosis Risk Loci Correlate with Cervical Cord Atrophy and May Explain the course of Disability," Neurogenetics, 16(3): 161-168, 2015.
Alfano, et al., "Automated Segmentation and Measurement of Global White Matter Lesion Volume in Patients with Multiple Sclerosis," *Journal of Magnetic Resonance Imaging*, 12(6): 799-807, 2000.
Amann, et al., "Subcortical brain segmentation of two dimensional T1-weighted data sets with FMRIB's Integrated Registration and Segmentation Tool (FIRST)," *NeuroImage Clinical*, 743-752, 2015.
Bagnato, et al., "T1 cortical hypointensities and their association with cognitive disability in multiple sclerosis," *Multiple Sclerosis*, 16(10): 1203-1212, 2010.
Bendfeldt, et al., "Longitudinal gray matter changes in multiple sclerosis—differential scanner and overall disease-related effects," *Human Brain Mapping*, 33(5): 1225-1245, 2012.
Bermel, et al., "Selective caudate atrophy in multiple sclerosis: a 3D MRI parcellation study," *Neuroreport*, 14(3): 335-339, 2003.
Boretius, et al., "Monitoring of EAE onset and progression in the common marmoset monkey by sequential high-resolution 3D MRI," *NMR in Biomedicine*, 19(1): 41-49, 2006.

(56) References Cited

OTHER PUBLICATIONS

Cao, "Directed Movement of Magnetic Nanoparticle-Loaded Immune Cells Using a Compact 3D Printed Chamber," Abstracts of Papers, 251st American Chemical Society National Meeting & Exposition, San Diego, CA Mar. 13-17, 2016, Coll-58.
Ceccarelli, et al., "A multiparametric evaluation of regional brain damage in patients with primary progressive multiple sclerosis," Human Brain Mapping, 30(9): 3009-3019, 2009.
Chen, et al., "Iron deposition of the deep grey matter in patients with multiple sclerosis and neuromyelitis optica: a control quantitative study by 3D-enhanced susceptibility-weighted angiography (ESWAN)," European Journal of Radiology, 81(4): e633-639, 2012.
Chu, et al., "Value of magnetization transfer imaging in judging microchanges lesions in normal-appearing white matter of multiple sclerosis," Zhong Yi Xue Za Zhi, 84(14): 1181-1185, 2004. (English Abstract).
Coebergh, et al., "Acute severe memory impairment as a presenting symptom of multiple sclerosis: a clinical case study with 3D double inversion recovery MR imaging," Multiple Sclerosis, 16(12): 1521-1524, 2010.
Cruccu, et al., "Trigeminal Neuralgia and Pain Related to Multiple Sclerosis," Pain, 143(3): 186-191, 2009.
De Graaf, et al., "Clinical application of multi-contrast 7-T MR imaging in multiple sclerosis: increased lesion detection compared to 3 T confined to grey matter," European Radiology, 23(2): 528-540, 2013.
Dell'Acqua, et al., Thalamocortical sensorimotor circuit in multiple sclerosis: an integrated structural and electrophysiological Assessment, Human Brain Mapping, 31(10): 1588-1600, 2010.
Dolezal, et al., "Detection of cortical lesions is dependent on choice of slice thickness in patients with multiple sclerosis," International Review of Neurobiology, 79475-79489, 2007.
Du, et al., "Iron deposition in the gray matter in patients with relapse-remitting multiple sclerosis: A longitudinal study using three-dimensional (3D)-enhanced T2*-weighted angiography (ESWAN)," European Journal of Radiology, 84(7): 1325-1332, 2015.
Edwards, et al., "Cognitive correlates of supratentorial atrophy on MRI in multiple sclerosis," Acta Neurologica Scandinavica, 104(4): 214-223, 2001.
Extended European Search Report Issued in Corresponding European Patent Application No. 17821341.9, dated Feb. 13, 2020.
Fartaria, et al., "Automated Detection of White Matter and Cortical Lesions in Early Stages of Multiple Sclerosis," Journal of Magnetic Resonance Imaging, 43(6): 1445-1454, 2016.
Filippi, et al., "Microstructural magnetic resonance imaging of cortical lesions in multiple sclerosis," Multiple Sclerosis, 19(4): 418-426, 2013.
Freifeld, et al., "Multiple Sclerosis Lesion Detection Using Constrained GMM and Curve Evolution," International Journal of Biomedical Imaging, Article ID 715124, 2009.
Gabr, et al., "Automated patient-specific optimization of three-dimensional double-inversion recovery magnetic resonance imaging," Magnetic Resonance in Medicine, 75(2): 585-593, 2016.
Gadeberg, et al., "How accurate are measurements on MRI? A study on multiple sclerosis using reliable 3D stereological methods," Journal of Magnetic Resonance Imaging, 10(1): 72-79, 1999.
Gobbi, et al., "Forceps Minor Damage and Co-Occurrence of Depression and Fatigue in Multiple Sclerosis," Multiple Sclerosis, 20(12): 1633-1640, 2014.
Guttmann, et al., "Multiple sclerosis lesion formation and early evolution revisited: A weekly high-resolution magnetic resonance imaging study," Multiple Sclerosis Journal, 1-9, 2015.
Hadhoum, et al., "Length of optic nerve double inversion recovery hypersignal is associated with retinal axonal loss," Multiple Sclerosis, 22(5): 649-658, 2016.
Hadjidemetriou, et al., "Computational Atlases of Severity of White Matter Lesions in Elderly Subjects with MRI," International Conference on Financial Cryptography and Data Security; [Lecture Notes in Computer Science; Lecture Notes Computer] Springer, Berlin, Heidelberg: 450-458, 2008.
Helms, et al., "High-resolution maps of magnetization transfer with inherent correction for RF inhomogeneity and T1 relaxation obtained from 3D Flash MRI," Magnetic Resonance in Medicine, 60(6): 1396-1407, 2008.
Hespel, "3D Printers Their Clinical, Experimental, and Teaching Uses," Available at: https://etd.auburn.edu/xmlui/bitstream/handle/10415/4764/Hespel%20Thesis%20.pdf.
Hildebrandt, et al., "Memory performance in multiple sclerosis patients correlates with central brain atrophy," Multiple Sclerosis, 12(4): 428-436, 2006.
Hofstetter, et al., "Progression in disability and regional grey matter atrophy in relapsing-remitting multiple sclerosis," Multiple Sclerosis, 20(2): 202-213, 2014.
Hosoya, et al., "Abducens nerve enhancement demonstrated by multi-planar reconstruction of contrast-enhanced three-dimensional MRI," Neuroradiology, 43(4): 295-301, 2001.
Ingrisch, et al., "Quantification of Perfusion and Permeability in Multiple Sclerosis: Dynamic Contrast-Enhanced MRI in 3D at 3T," Investigative Radiology, 47(4): 252-258, 2012.
Jimenez, et al., "A Web platform for the interactive visualization and analysis of the 3D fractal dimension of MRI data," Journal of Biomedical Informatics, 51: 51176-51190, 2014.
Kassubek, et al., "Age-related brain parenchymal fraction is significantly decreased in young multiple sclerosis patients: a quantitative MRI study," Neuroreport, 14(3): 427-430, 2003.
Kearney, et al., "Grey matter involvement by focal cervical spinal cord lesions is associated with progressive multiple sclerosis," Multiple Sclerosis, 22(7): 910-920, 2016.
Kirov, et al., "Serial proton MR spectroscopy of gray and white matter in relapsing-remitting MS," Neurology, 80(1): 39-46, 2013.
Kitzler, et al., "Deficient MWF mapping in multiple sclerosis using 3D whole-brain multi-component relaxation MRI," NeuroImage, 59(3): 2670-2677, 2012.
Kolber, et al., "Identification of Cortical Lesions Using DIR and FLAIR in Early Stages of Multiple Sclerosis," Journal of Neurology, 262(6): 1473-1482, 2015.
Kondo, "A Neurosurgical Simulation of Skull Base Tumors Using a 3D Printed Rapid Prototyping Model Containing Mesh Structures," Acta Neurochurugica, 2016.
Lavigne, et al., "3D+t brain MRI segmentation using robust 4D Hidden Markov Chain," IEEE Engineering in Medicine and Biology Society, Annual Conference, 2014.
Maarouf, et al., "Topography of Brain Sodium Accumulation in Progressive Multiple Sclerosis," Magnetic Resonance Materials in Physics, Biology and Medicine, 27(1): 53-62, 2014.
Matthews, "The OPTIMISE Data Project: Toward Improving Multiple Sclerosis Treatment," Future Neurology, 10(3): 187-190, 2015.
Mills, et al., "3D MRI in multiple sclerosis: a study of three sequences at 3 T," The British Journal of Radiology, 80(953): 307-320, 2007.
Moraal, et al., "Multi-contrast, isotropic, single-slab 3D MR imaging in multiple sclerosis," European Radiology, 18(10): 2311-2320, 2008.
Neema, et al., "3 T MRI relaxometry detects T2 prolongation in the cerebral normal-appearing white matter in multiple sclerosis," NeuroImage, 46(3): 633-641, 2009.
Nelson, et al., "Is 3D MPRAGE better than the combination DIR/PSIR for cortical lesion detection at 3T MRI?" Multiple Sclerosis and Related Disorders, 3(2): 253-257, 2014.
Nessler, et al., "Early MRI changes in a mouse model of multiple sclerosis are predictive of severe inflammatory tissue damage," Brain—A Journal of Neurology, 130(Pt 8) 2186-2198, 2007.
Newbould, et al., "Age independently affects myelin integrity as detected by magnetization transfer magnetic resonance imaging in multiple sclerosis," NeuroImage Clinical, 4: 641-648, 2014.
Noth, et al., "Perfluoro-15-crown-5-ether labeled macrophages in adoptive transfer experimental allergic encephalomyelitis," Artificial Cells, Blood Substitutes, and Immobilization Biotechnology, 25(3): 243-254, 1997.

(56) References Cited

OTHER PUBLICATIONS

Oishi, et al., "Interactive Presurgical Simulation Applying Advanced 3D Imaging and Modeling Techniques for Skull Base and Deep Tumors," *Journal of Neuroscience*, 119: 94-105, 2013.
Palma, et al., "A Novel Multiparametric Approach to 3D Quantitative MRI of the Brain," *PLOS One*, 10(8): e0134963, 2015.
Paniagua, et al., "A comparative MRI study for white matter hyperintensities detection: 2D-FLAIR, FSE PD 2D, 3D-FLAIR and FLAIR MIP," *British Journal of Radiology*, 87(1035): 2014.
Pareto, et al., "Lesion filling effect in regional brain volume estimations: a study in multiple sclerosis patients with low lesion load," *Neuroradiology*, 58(5): 467-474, 2016.
Rahman, et al., "A comparative study of magnetic resonance venography techniques for the evaluation of the internal jugular veins in multiple sclerosis patients," *Magnetic Resonance Imaging*, 31(10): 1668-1676, 2013.
Ramasamy, et al., "Effect of Met66 allele of the BDNF rs6265 SNP on regional gray matter volumes in patients with multiple sclerosis: A voxel-based morphometry study," Pathophysiology, The Official Journal of the International Society of Pathophysiology, 18(1): 53-60, 2011.
Ramasamy, et al., "Extent of cerebellum, subcortical and cortical atrophy in patients with MS: a case-control study," *Journal of the Neurological Sciences*, 282(1-2): 47-54, 2009.
Riemer, et al., "Sodium (23Na) Ultra-Short Echo Time Imaging in the Human Brain Using a 3d-Cones Trajectory," *Magnetic Resonance Materials in Physics, Biology and Medicine*, 27(1): 35-46, 2014.
Rousseau, et al., "An a contrario approach for change detection in 3D multimodal images: application to multiple sclerosis in MRI," *IEEE Engineering in Medicine and Biology Society*, Annual Conference, 2069-2072, 2007.
Rumzan, et al., "Iron deposition in the precentral grey matter in patients with multiple sclerosis: a quantitative study using susceptibility-weighted imaging," *European Journal of Radiology*, 82(2): e95-99, 2013.
Sastre-Garriga, et al., "Grey and white matter volume changes in early primary progressive multiple sclerosis: a longitudinal study," *Brain—A Journal of Neurology*, 128(Pt. 6): 1454-1460, 2005.
Seewann, et al., "Postmortem verification of MS cortical lesion detection with 3D DIR," *Neurology*, 78(5): 302-308, 2012.
Sharma & Marikkannu, "Hybrid RGSA and Support Vector Machine Framework for Three-Dimensional Magnetic Resonance Brain Tumor Classification," *The Scientific World Journal*, Article ID 184350, 2015.
Spring, et al., "Sexual dimorphism revealed in the structure of the mouse brain using three-dimensional magnetic resonance imaging," *NeuroImage*, 35(4): 1424-1433, 2007.
Stadie, et al., "Virtual Reality System for Planning Minimally Invasive Neurosurgery," *Journal of Neurosurgery*, 108(2): 382-394, 2008.
Tardif, et al., "Quantitative Magnetic Resonance Imaging of Cortical Multiple Sclerosis Pathology," *Multiple Sclerosis International*, 742018, 2012.
Tinelli, et al., "Structural brain MR imaging changes associated with obsessive-compulsive disorder in patients with multiple sclerosis," *American Journal of Neuroradiology*, 34(2): 305-309, 2013.
Tsai, et al., "Practical Aspects of Shortening Acquisition Time in Brain MR Susceptibility-Weighted Imaging," *The Neuroradiology Journal*, 25(6): 649-656, 2012.
Tubridy, et al., "Three-dimensional fast fluid attenuated inversion recovery (3D fast FLAIR): a new MRI sequence which increases the detectable cerebral lesion load in multiple sclerosis," *The British Journal of Radiology*, 71(848): 840, 845, 1998.
Turner, et al., "Cerebral atrophy and disability in relapsing-remitting and secondary progressive multiple sclerosis over four Years," *Multiple Sclerosis*, 9(1): 21-27, 2003.
Utriainen, et al., "Using magnetic resonance imaging as a means to study chronic cerebral spinal venous insufficiency in multiple sclerosis patients," *Techniques in Vascular and Interventional Radiology*, 15(2): 101-112, 2012.
Vakharia, et al., "Review of 3-Dimensional Printon on Cranial Neurosurgery Simulation Training," *World Neurosurgery*, 88: 188-198, 2016.
Vinitski, et al., "Fast tissue segmentation based on a 4D feature map in characterization of intracranial lesions," *Journal of Magnetic Resonance Imaging*, 9(6): 768-776, 1999.
Waran, et al., "Utility of Multimaterial 3D Printers in Creating Models with Pathological Entities to Enhance the Training Experience of Neurosurgeons," *Journal of Neurosurgery*, 120(2): 489-492, 2014.
Xu, et al., Study of relapsing remitting experimental allergic encephalomyelitis SJL mouse model using MION-46L enhanced in vivo MRI: early histopathological correlation, *Journal of Neuroscience Research*, 52(5): 549-558, 1998.
Yarnykh, "Pulsed Z-spectroscopic imaging of cross-relaxation parameters in tissues for human MRI: theory and clinical applications," *Magentic Resonance in Medicine*, 47(5): 929-939, 2002.
Zhang, et al., "Longitudinal change in magnetic susceptibility of new enhanced multiple sclerosis (MS) lesions measured on serial quantitative susceptibility mapping (QSM)," *Journal of Magnetic Resonance Imaging*, 44(2): 2016.
Goldberg-Zimring et al., "Assessment of Multiple Sclerosis Lesions with Spherical Harmonics: Comparison of MR Imaging and Pathologic Findings" *Radiology*, 2005, 235(3), 1036-1044.
Newton et al., "P1603 3-dimensional shape and surface characteristics differentiate multiple sclerosis lesions from other etiologies." *Multiple Sclerosis Journal*, Sep. 14, 2016, 22(S3), 845-846.
Newton et al., "Three-Dimensional Shape and Surface Features Distinguish Multiple Sclerosis Lesions from Nonspecific White Matter Disease" *J Neuroimaging*, May 10, 2017, 27, 613-619.
Response under Rules 70(2) and 70a to the Extended European Search Report issued in Corresponding European Application No. 17821341.9, dated Sep. 14, 2020.
Despotović et al., "MRI Segmentation of the Human Brain: Challenges, Methods, and Applications" *Computational and Mathematical Methods in Medicine* 2015, 2015, 1-23.
Office Action issued in Corresponding European Application No. 17821341.9, dated Apr. 6, 2021.

\* cited by examiner

METHODS, APPARATUSES, AND SYSTEMS FOR CREATING 3-DIMENSIONAL REPRESENTATIONS EXHIBITING GEOMETRIC AND SURFACE CHARACTERISTICS OF BRAIN LESIONS

CROSS-REFERENCE TO RELATED APPLICATION

This application is a national phase application under 35 U.S.C. § 371 of International Application No. PCT/US2017/040229, filed Jun. 30, 2017 which claims priority to U.S. Provisional Patent Application 62/357,477 filed Jul. 1, 2016, the content of each is incorporated herein by reference in its entirety.

BACKGROUND

1. Field of the Invention

This disclosure relates generally to methods, apparatuses, and systems for creating 3-dimensional (3D) representations exhibiting geometric and surface characteristics of brain lesions.

2. Description of Related Art

The diagnosis of multiple sclerosis (MS) requires the fulfillment of both clinical and radiological criteria. This may include a determination of key radiological tenets such as a requisite number of lesions having a specific character (i.e. size, shape, and morphology) and spatial distribution patterns with involvement of periventricular, juxtacortical, infratentorial, and spinal cord regions. The effective application of the existing dissemination in space criteria may be hindered by the highly sensitive nature of magnetic resonance imaging (MRI) technology, the heterogeneity of lesions resulting from a variety of medical conditions, concomitant radiological features resulting from age-related changes and disease, and the lack of additional radiological characteristics beyond 2-dimensional (2D) descriptions.

At present, the diagnosis of MS is usually made through the use of 2D MRI images. The implementation of certain imaging metrics, including the use of quantitative phase imaging, has improved lesion specificity. This may highlight the presence of central vasculature within lesions and distinct peripheral rings, suggesting the presence of iron within macrophages. The use of fluid-attenuated inversion recovery (FLAIR) MRI at 3 Tesla (T) and T2-weighted and susceptibility weighted imaging (SWI) at 7 T in larger patient groups has also been utilized to better characterize MS from non-MS lesions. A previously identified threshold of >40% was described for improving the specificity of MS lesions. However, this technique has been limited by the lack of appreciation of the central vessel in all orthogonal planes of view and the abundance of vessels intersecting lesions within the supratentorial region. Beyond these efforts, peripheral regions of hypointensity, presumed to be related to the presence of iron within macrophages, have also been described in MS patients.

SUMMARY

This disclosure includes embodiments that allow for the depiction of MRI brain lesions in true 3-dimensional (3D) form. This approach may isolate lesions resulting from patients with multiple sclerosis and those with non-specific white matter disease changes due to normal aging, migraine headaches, high blood pressure, smoking, and other vascular risk factors. By isolating and evaluating brain lesions in actual 3D form, in comparison to conventional 2D approaches that provide slice-by-slice renditions of 3D shapes, the disclosed embodiments may enable a better understanding of both lesion shapes and surface features in vivo and new descriptive characteristics may be generated based on the findings between groups. The unique approach of the disclosed embodiments represents a scientific effort aimed at redefining the shapes and surface features of MS lesions compared with those resulting from one of the most common disease states responsible for white matter injury within the brain—non-specific white matter (NSWM) disease. Beyond geometric shape and surface characteristics, the disclosed embodiments may also provide a more accurate assessment of lesion sizes, volumes, and surface areas when compared to existing technology.

This disclosure includes embodiments of methods, apparatuses, and systems for creating 3D representations exhibiting at least one geometric characteristic and/or at least one surface characteristic of brain lesions. Some embodiments comprise a system that may include a computer system having at least one processor that may be configured to receive one or more 3D images of a brain. The computer system may be able to enable an identification of one or more brain lesions in the one or more 3D images of the brain and enable a segmentation of the one or more 3D images. In some embodiments, the segmentation may enable an isolation of the one or more brain lesions. The computer system may be further configured to enable a creation of one or more 3D brain lesion images based on the segmentation. The one or more 3D brain lesion images may comprise one or more lesion characteristics. The computer system may further enable a comparison of the one or more lesion characteristics of the one or more 3D brain lesion images with one or more predetermined lesion characteristics, enable a determination of a type of the one or more brain lesions based on a match between the one or more lesion characteristics of the one or more 3D brain lesion images with one or more of the predetermined lesion characteristics, and enable the sending of 3D representation data corresponding to the one or more 3D brain lesion images, the 3D representation data configured to enable a creation of one or more physical 3D representations of the one or more brain lesions. In some embodiments, the at least one processor may be able to communicate with a memory source and/or non-transitory computer readable medium to receive one or more instructions enabling the at least one processor to perform the actions disclosed above. In some embodiments, the at least one processor may be actively performing the actions disclosed above based on one or more instructions received from a memory source and/or non-transitory computer readable medium. In some embodiments, the at least one processor may be hardwired in such a way as to have the ability to perform and/or actually perform the actions disclosed above.

In some embodiments, the computer system may be further configured to receive one or more 2D images of a brain and enable a creation of one or more 3D images of the brain based on the one or more 2D images of the brain. The one or more 3D images may comprise one or more maximum intensity projection (MIP) images that may be configured to enable 3D spatial visualization of the brain. In some embodiments, the one or more 3D brain lesion images may comprise one or more orthographic projections in stereolithographic format. In some embodiments, the one or more physical 3D representations comprise fused filament 3D printed models. The one or more 3D images of the brain may comprise one or more isotropic MRI images. In some embodiments, the one or more lesion characteristics may comprise one or more of geometric characteristics and surface characteristics. The one or more geometric characteristics may comprise one or more of a symmetry characteristic, a surface morphology characteristic, a lobular shape characteristic, a protrusion characteristic, a slope characteristic, a tapered shape characteristic, a spherocylindrical shape characteristic, or the like. The one or more surface characteristics may comprise one or more of a surface topography characteristic, a surface irregularity characteristic, a surface area to volume ratio characteristic, a distribution of mass characteristic, or the like. In some embodiments, the one or more predetermined lesion characteristics may correspond to one or more lesion characteristics associated with one or more disease etiologies. The one or more disease etiologies may comprise one or more of MS and non-specific categories such as aging, migraine headache, small vessel disease, cryptogenic white matter, or the like. In some embodiments, the one or more 3D brain lesion images may include one or more lesion vasculature characteristics.

Some embodiments of the present methods include a method of creating 3D representations of brain lesions that may comprise receiving, by a computer system comprising at least one processor, one or more 3D images of a brain; enabling, by the computer system, an identification of one or more brain lesions in the one or more 3D images of the brain; enabling, by the computer system, a segmentation of the one or more 3D images, the segmentation enabling an isolation of the one or more brain lesions; enabling, by the computer system, a creation of one or more 3D brain lesion images based on the segmentation, the one or more 3D brain lesion images comprising one or more lesion characteristics; enabling, by the computer system, a comparison of the one or more lesion characteristics of the one or more 3D brain lesion images with one or more predetermined lesion characteristics; enabling, by the computer system, a determination of a type of the one or more brain lesions based on a match between the one or more lesion characteristics of the one or more 3D brain lesion images with one or more of the predetermined lesion characteristics; and enabling, by the computer system, the sending of 3D representation data corresponding to the one or more 3D brain lesion images, the 3D representation data configured to enable a creation of one or more physical 3D representations of the one or more brain lesions.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

DETAILED DESCRIPTION OF ILLUSTRATIVE EMBODIMENTS

At present, the appreciation of structural anomalies originating from in situ demyelination or non-specific changes within white matter due to aging, migraine headaches, or small vessel disease is limited by traditional 2-dimensional, forced perspective views of T2-hyperintensities within brain tissue acquired from MRI studies deficient in full coverage of the brain. In addition, the associated surface characteristics of lesions originating from MS or other etiologies are currently unknown. Therefore, 3D data from observed T2-hyperintensities may provide better lesion characterization, allowing for better differentiation of anomalies arising from MS compared to other etiologies. This approach may also allow for better characterization of non-specific white matter lesions. This may reduce the over-diagnosis of MS by healthcare professionals, thereby preventing the over utilization of disease modifying therapies and their associated morbidities and high costs.

The embodiments discussed below describe systems, apparatus, and methods for creating 3D representations exhibiting shape and surface characteristics of brain lesions. More specifically, the embodiments discussed below present 3D spatial visualization, lesion surface, and geometric and surface characteristic data of MS lesions in comparison to other disease states that may improve lesion specificity by leveraging imaging techniques that can be implemented into clinically acquired studies for direct clinical application. The embodiments discussed below also describe integrating the use of 3D printing software and hardware, allowing for tactile review of the observed findings on MRI to further elucidate the geometric and surface characteristics between varying etiologies.

Figure 1:
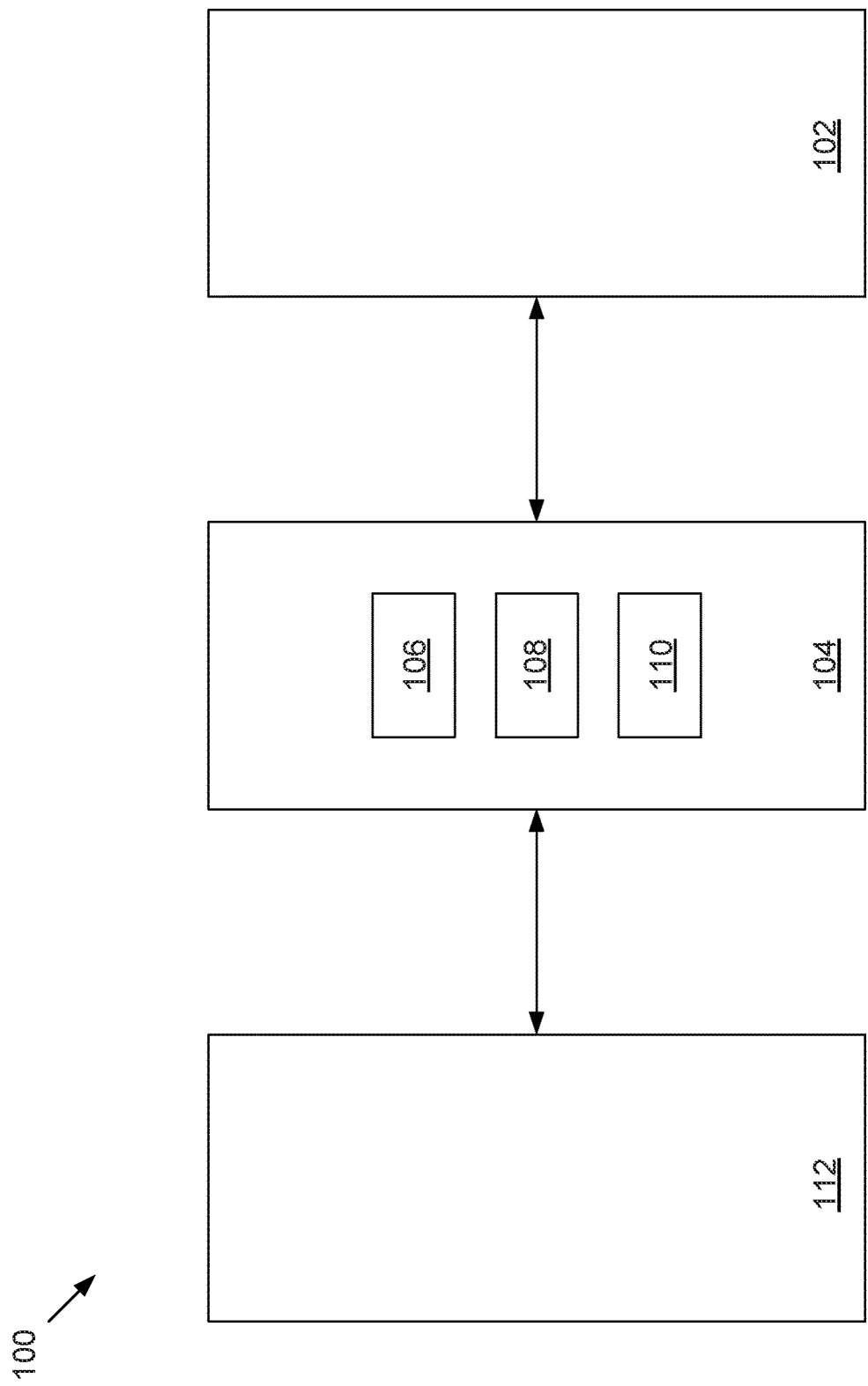
FIG. 1 depicts an exemplary 3D imaging and brain lesion representation system according to an embodiment of the disclosure.

Referring now to the drawings, FIG. 1 depicts an exemplary 3D imaging and brain lesion representation system 100 according to an embodiment of the disclosure. In the embodiment shown, an MRI device 102 may be provided. The MRI device 102 may be a 2D MRI device, a 3D MRI device, or one or more MRI devices providing both 2D and 3D imaging capabilities. A processing device 104 may be capable of receiving 2D and/or 3D images taken by the MRI device. Processing device 104 may be a part of a computer system that may include standard components such as a hard drive, monitor, printer, keyboard, and mouse, among others, that may enable a user to interact with the processing device 104. In the embodiment shown, processing device 104 may include one or more of a segmentation application 106, a 3D imaging application 108, and one or more databases 110. In some embodiments, segmentation application 106 may be configured to receive one or more MRI images from MRI device 102, segment the one or more MRI images into one or more regions, and enable a selection of one or more regions. These selected regions may be referred to as regions of interest (ROI). In some embodiments, the selection of ROI may be done automatically by processing device 104. In some embodiments, the selection of ROI may be done by a user.

In some embodiments, the selected ROI may be exported by segmentation application 106 and imported into 3D image application 108. In some embodiments, 3D image application 108 may generate one or more 3D MIP images of the selected ROI. In some embodiments, the selected ROI may correspond to one or more focal brain lesions. In some embodiments, the selected ROI may be converted to stereolithography (.stl) format and/or displayed as 3D orthographic images to enable orthographic views. The one or more 3D images may be displayed to a user and 3D image application 108 may enable a user to view and manipulate the one or more 3D images. In some embodiments, image manipulation capabilities may include capabilities to rotate, zoom, mark, color, and select the one or more images. In some embodiments, one or more databases 110 may contain information corresponding to various brain lesion characteristics. Examples of these brain lesion characteristics may include shape or geometric characteristics, size characteristics, topographical characteristics, volume characteristics, surface area characteristics and the like. In some embodiments, the brain lesion characteristics may be associated with one or more etiologies. Examples of these etiologies may include MS, aging, small vessel disease, migraine headaches, and other non-specific white matter lesion etiologies. In the embodiment shown, processing device 104 may be configured to send data corresponding to the one or more 3D images to a 3D printing device 112. 3D printing device 112 may create a 3D physical representation of the received one or more 3D images.

Figure 2:
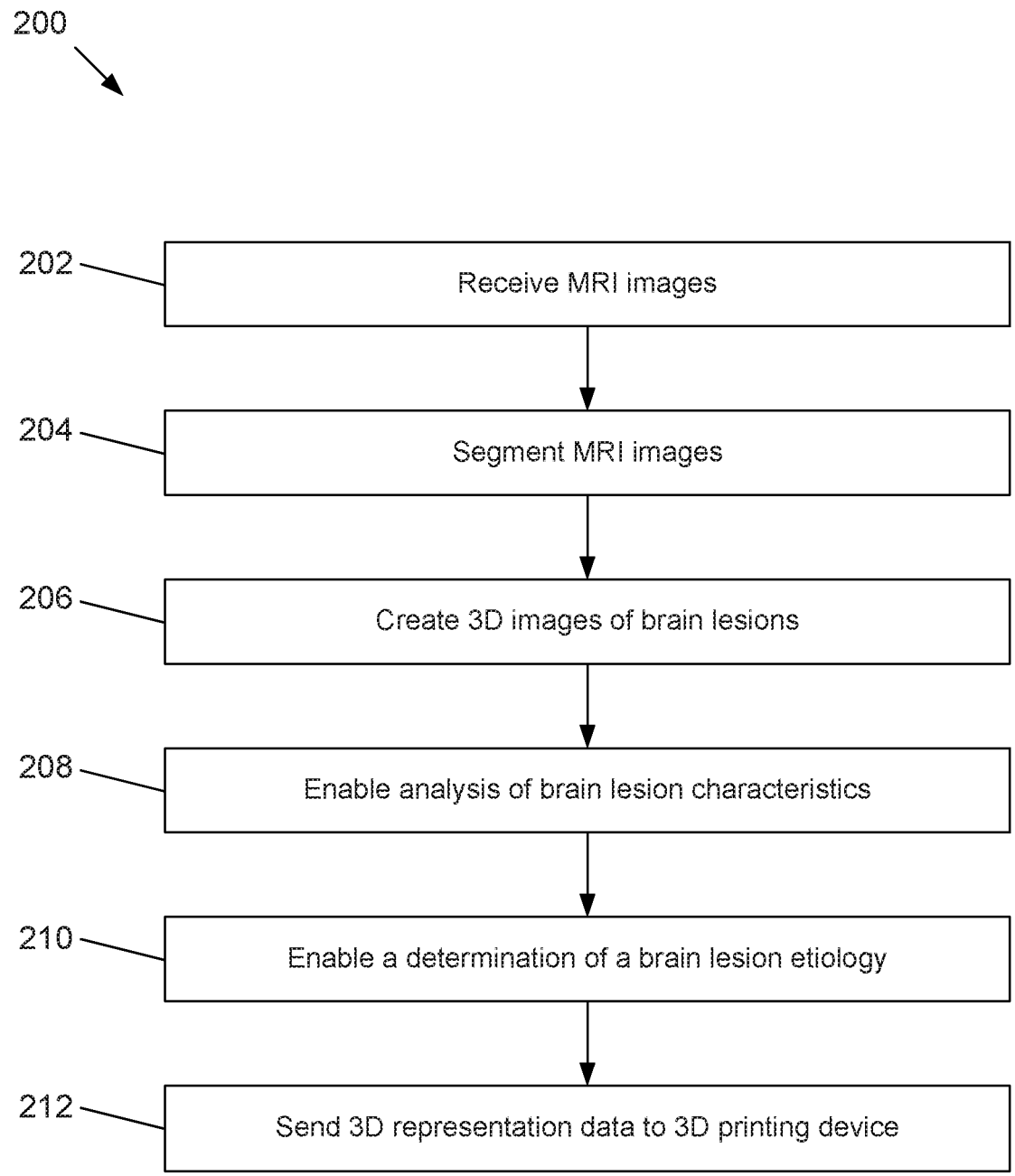
FIG. 2 depicts an exemplary method for creating 3D representations of brain lesions according to an embodiment of the disclosure.

FIG. 2 depicts an exemplary method 200 for creating 3D representations of brain lesions according to an embodiment of the disclosure. In one embodiment of the disclosure, method 200 may be implemented by system 100. In the embodiment shown in FIG. 2, method 200 may begin at step 202 by receiving one or more 2D or 3D MRI images. In some embodiments, 3D MRI images may be created from one or more received 2D MRI images. Method 200 may continue at step 204 by segmenting the received one or more MRI images. In some embodiments, segmenting step 204 may include segmenting the one or more MRI images into one or more ROI. The one or more ROI may correspond to one or more brain lesions. In some embodiments, lesions may be selected in 3D format using an MIP 3D file. In this way, the computer system and/or a user may manipulate a 3D object in 2D space and may select one or more ROI. Isolating lesions from 3D MRI images may allow for a better appreciation of both the geometric and surface characteristics of brain lesions. In a 2D view, a variety of signals may influence pixel intensities that may result in pixel misclassification. Isolating lesions from 3D images may overcome some of these shortcomings of 2D lesion isolation.

Method 200 may continue at step 206 by creating one or more 3D images of brain lesions. In some embodiments, the one or more 3D brain lesion images may be orthographic images or MIP images. Method 200 may continue at step 208 by enabling the analysis of one or more brain lesion characteristics. For example, a computer system may analyze the one or more brain lesion images to determine one or more characteristics of the brain lesion. A user may also analyze the one or more brain lesion images by interacting with the computer system. In some embodiments, metadata may be used to denote a type or category of a brain lesion characteristic. In some embodiments, brain lesion characteristics may include geometric characteristics. Geometric characteristics may provide insights into a size and shape of a brain lesion. Examples of geometric characteristics may include lesion symmetry/asymmetry, surface morphology (e.g., amorphous, ovoid), the existence of lobes and/or protrusions, and other shape characteristics (e.g., tapered/wedge, spherocylindrical). In some embodiments, brain lesion characteristics may include surface characteristics. Surface characteristics may provide insights into lesion surface traits and lesion properties not associated with geometry. Examples of surface characteristics may include the existence of surface microstructures, surface topography (e.g., steepness/sheerness of surface peaks and valleys), surface irregularities, and a non-uniform distribution of mass of the lesion. In some embodiments, the computer system may engage in machine learning to generate descriptive surface, shape, and signal characteristics from the entire lesion or sections within lesions in order to more efficiently and accurately classify lesion types.

Method 200 may continue at step 210 by enabling a determination of a brain lesion etiology. In some embodiments, a computer system may compare the one or more brain lesion characteristics to one or more previously stored brain lesion characteristics to determine possible matches. In some embodiments, one or more previously stored brain lesion characteristics may correspond to one or more brain lesion etiologies. In instances where the analyzed one or more brain lesion characteristics match one or more previously stored brain lesion characteristics, the computer system may determine one or more possible etiologies of the one or more brain lesions. In some embodiments, a user may be able to determine one or more possible etiologies of the one or more brain lesions based on each of their one or more brain lesions characteristics. Method 200 may continue at step 212 by sending data corresponding to the one or more 3D brain lesion images to a 3D printing device. Based on the received data, the 3D printing device may create a 3D physical representation or printed model of a brain lesion. In some embodiments, the 3D physical representation may exhibit one or more of the brain lesion characteristics. A user may use the 3D physical representation as an additional tool to help the user determine an etiology of the brain lesion.

Figure 3:
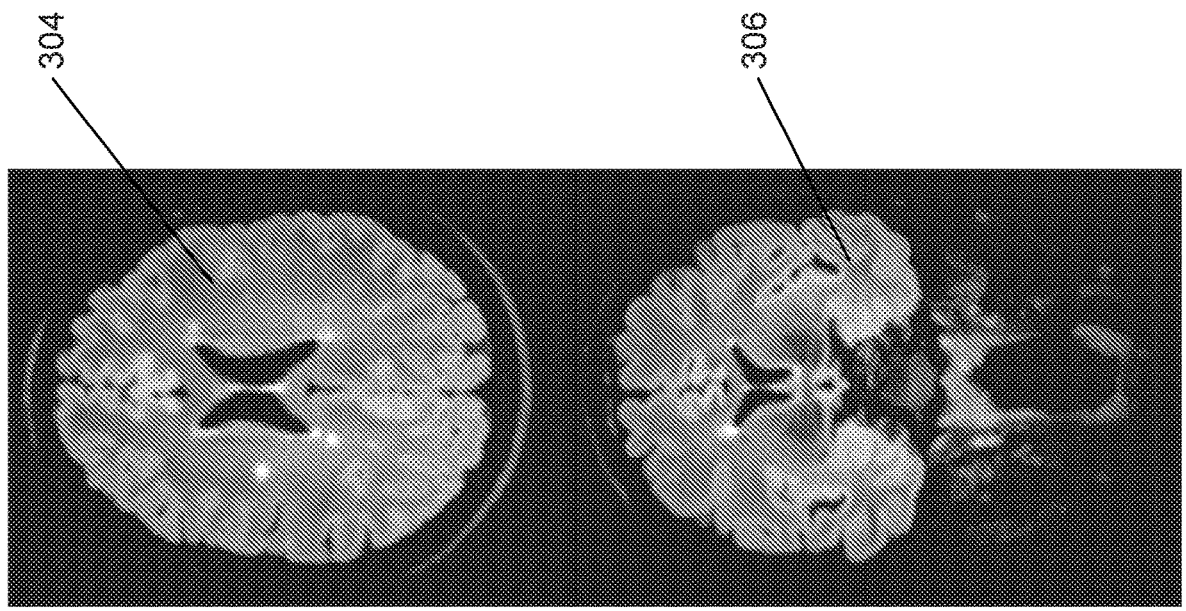
FIG. 3 depicts exemplary 2D MRI images that may be received according to an embodiment of the disclosure.
Figure 3:
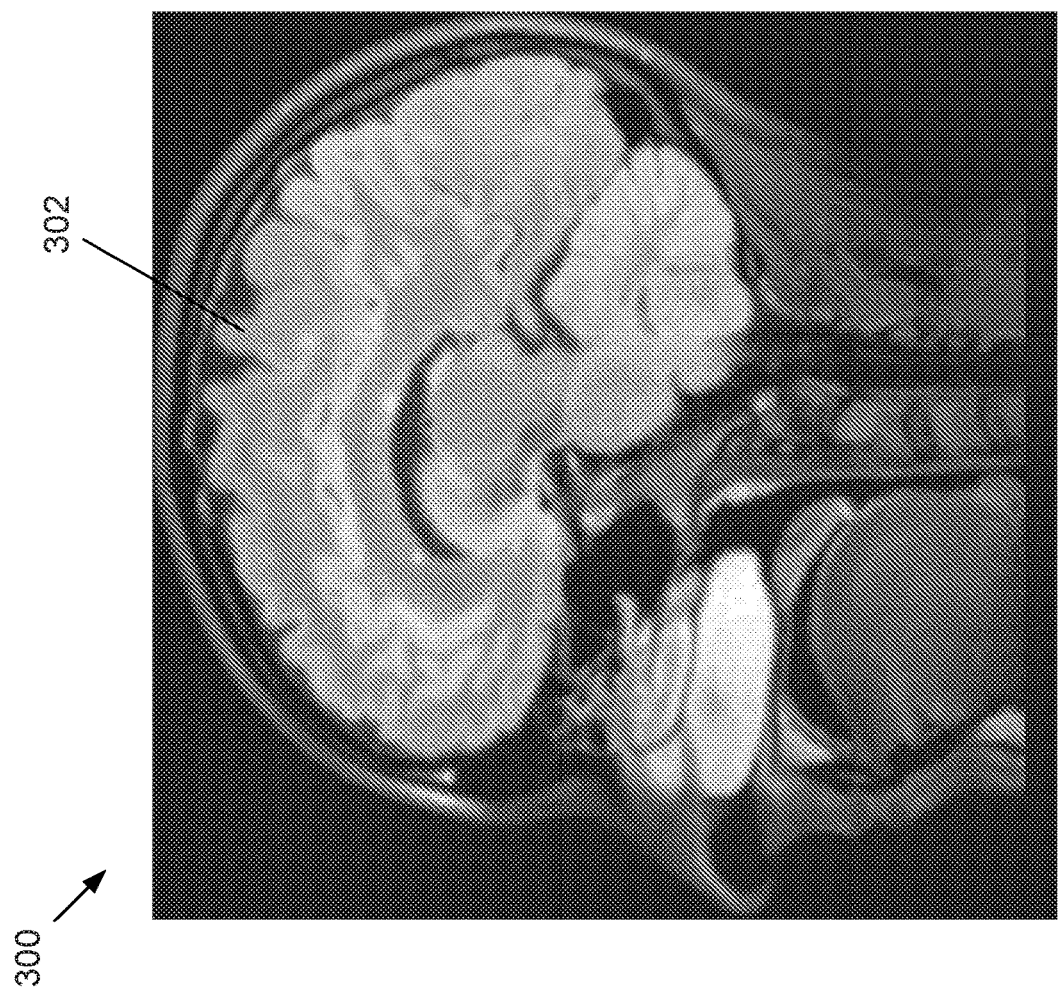

FIG. 3 depicts exemplary 2D MRI images 300 that may be received according to an embodiment of the disclosure. 2D MRI images may provide multiple views from different imaging angles. For example, a sagittal image 302, an axial image 304, and a coronal image 306 may be provided. In many traditional methods, 2D MRI images have been used to diagnose the existence of brain lesions. In some embodiments of the disclosure, 2D MRI images may be received by a computing system and used to construct representative 3D images.

Figure 4:
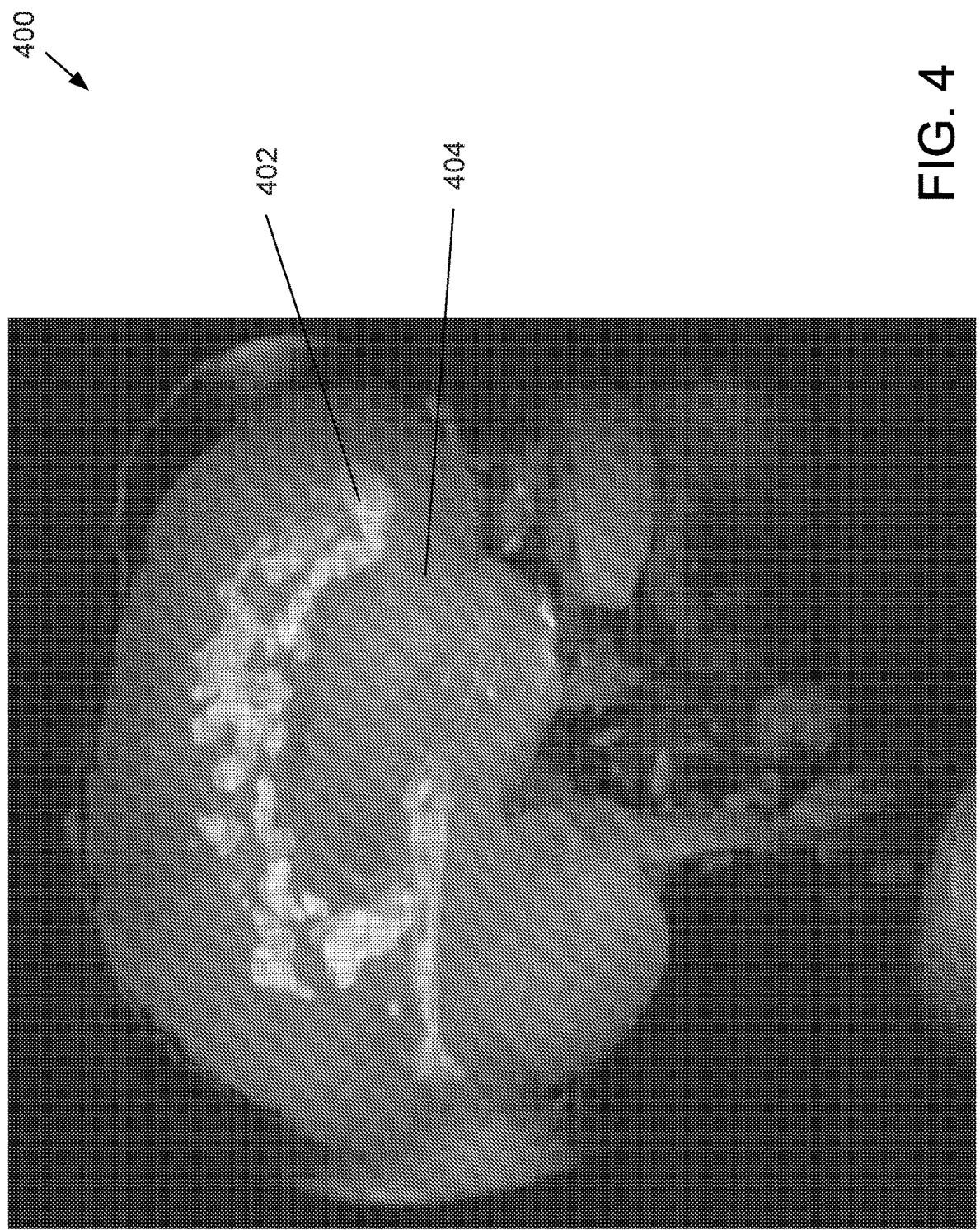
FIG. 4 depicts an exemplary 3D MRI image that may be received or constructed according to an embodiment of the disclosure.

FIG. 4 depicts an exemplary 3D MRI image 400 that may be received or constructed according to an embodiment of the disclosure. In some embodiments, 3D MRI image may be constructed by a computing system from one or more received 2D MRI images. In other embodiments, 3D MRI images may be received by a computing system from an MRI system having 3D imaging capabilities. In the embodiment shown, 3D MRI image 400 shows one or more brain lesions 402 that may be depicted in one or more shades of white and shows areas of healthy brain tissue 404 that may be depicted in one or more shades of gray. This may assist a user viewing the image to distinguish brain lesions from healthy brain tissue. In some embodiments, 3D MRI image 400 may be configured to be accessed and/or manipulated by a user. In some embodiments, the user may be able to rotate, zoom, mark, color, and select areas of the 3D MM image 400. In some embodiments, a computer system may perform a segmentation process on 3D MM image 400 that may segment 3D MRI image 400 into one or more ROI. A brain lesion 402 may be selected by the computer system or the user and may be denoted or saved as a ROI.

Figure 5:
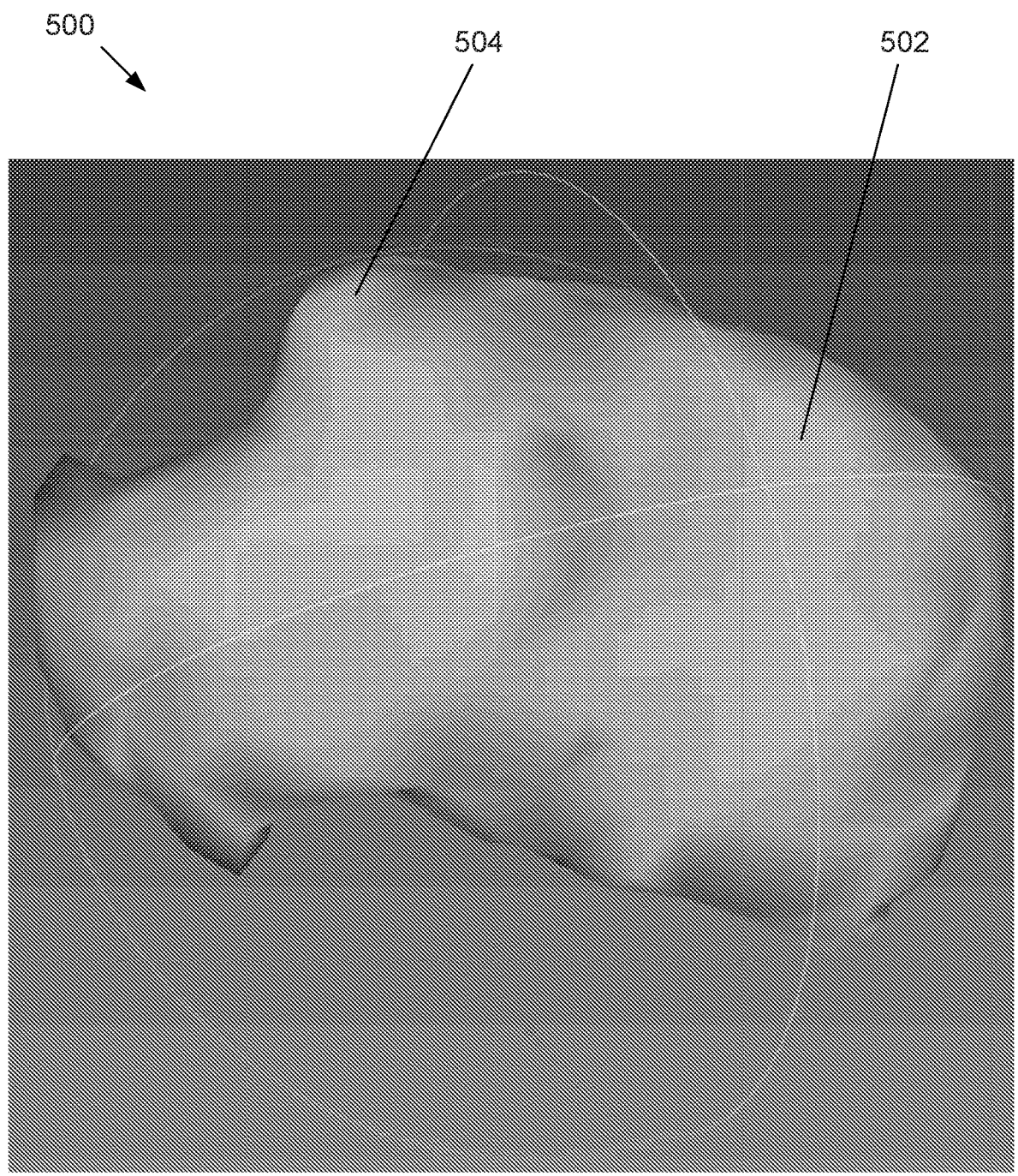
FIG. 5 depicts an exemplary 3D brain lesion image that may be constructed according to an embodiment of the disclosure.
Figure 6:
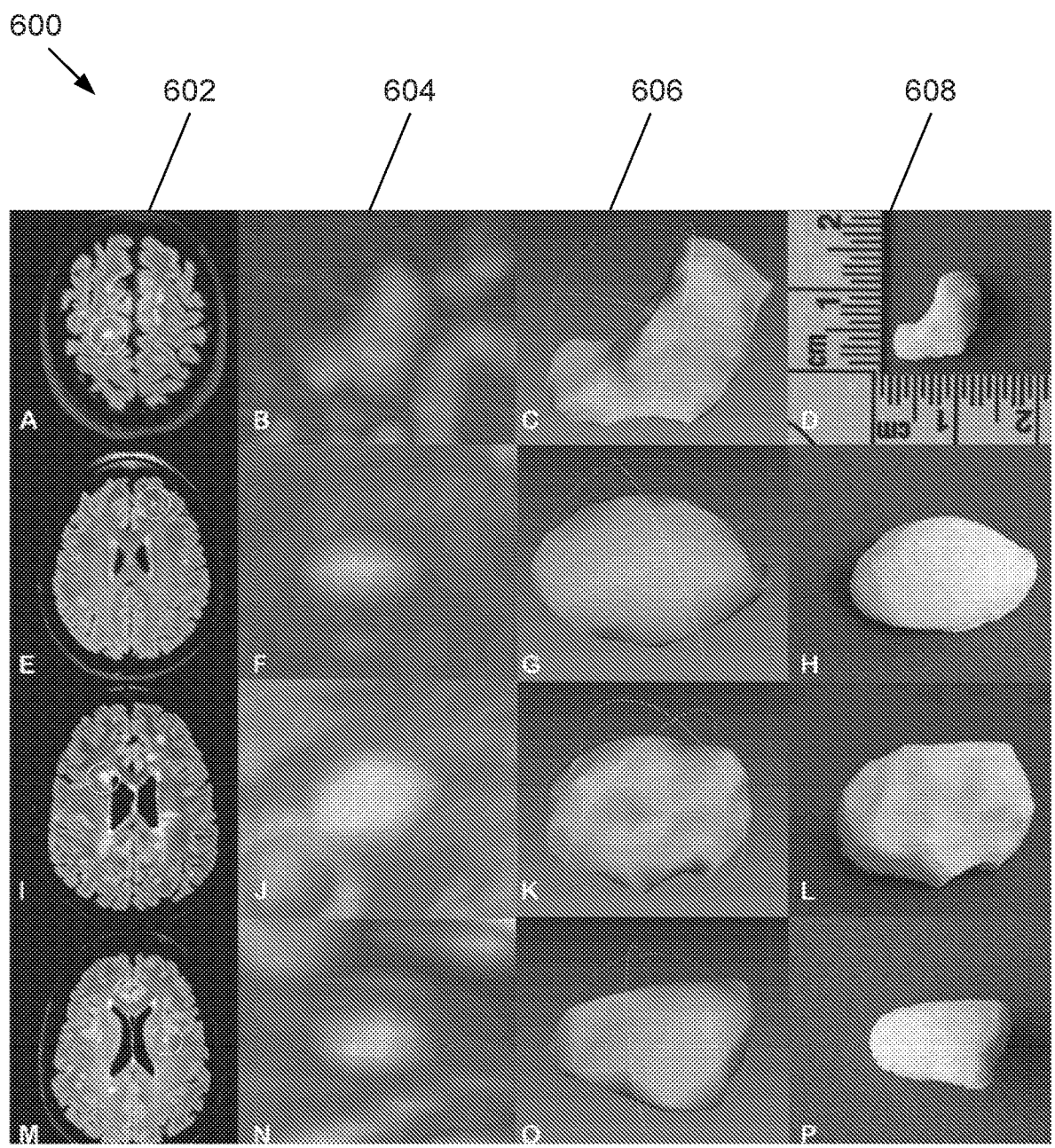
FIG. 6 depicts exemplary experimental results from an implementation of the systems and methods described by an embodiment of the disclosure.

FIG. 5 depicts an exemplary 3D brain lesion image 500 that may be constructed according to an embodiment of the disclosure. In the embodiment shown, 3D brain lesion image 500 may depict a brain lesion 502 and one or more brain lesion characteristics 504, such as a round protuberance existing on a particular surface of the brain lesion. In some embodiments, 3D brain lesion image 500 may be an MIP image. In some embodiments, 3D brain lesion image 500 may be an orthogonal image generated from one or more selected ROI that provides orthogonal views to a user. 3D brain lesion image 500 may also be in stereolithography format. In some embodiments, 3D brain lesion image 500 may provide a 3D spatial visualization of the brain legion and may be configured to be accessed and/or manipulated by a user. In some embodiments, the user may be able to rotate, zoom, mark, color, and select areas of the 3D brain lesion image 500. As discussed above, one or more brain lesion characteristics 504 may be displayed. In some embodiments, data related to lesion characteristics such as size (e.g., x, y, and z planes), volume, surface area, surface area to volume ratio, volume to surface area ratio, topographical surface characteristics, geometric characteristics, and the like may be acquired from the 3D MRI image 400 by the computer system in order to depict brain lesion 502 and brain lesion characteristics 504 as accurately as possible. In some embodiments, differing signal intensities determined from MRI images may be used to determine surface texture of the lesion. For example, a signal intensity corresponding to a protrusion on a lesion surface may have a different intensity from a signal corresponding to a flat surface or an indented surface of the lesion. Due to the accuracy of the 3D brain lesion image 500, the computer system and/or the user may more efficiently and accurately determine an etiology of the brain lesion.

FIGS. 6-9 depict exemplary experimental results from implementations of the systems and methods described by the embodiments of the disclosure. In order to test the disclosed embodiments, a series of tests were performed on recruited patients who were placed into two test groups. The patients in one group of patients each had an established diagnosis of MS based on a comprehensive medical evaluation by fellowship trained MS specialists. These patients had a confirmed diagnosis of MS based on established criteria, results from supporting para-clinical studies (such as abnormal cerebrospinal fluid profiles, electrophysiological abnormalities, and the like) and the exclusion of other disease states. The other group of patients consisted of confirmed non-MS patients with a history of migraine headaches or small vessel disease with abnormal brain MRI findings affecting supratentorial white matter. These patients had a history of brain anomalies atypical for in situ demyelination based on the formal imaging interpretations by a board certified neuroradiologist and clinical impressions by specialists in MS, and further supported by negative laboratory or other para-clinical studies to identify a clear underlying etiology.

Standardized brain MRI studies were performed on all study participants and all analyses implemented without knowledge of clinical history, current or past treatments, or disease duration. For the embodiments shown, the imaging studies were performed on a 3T MRI scanner using a 32-channel phased array coil in reception and body coil in transmission. Each MRI imaging study included one or more scout localizers, a 3D high-resolution inversion recovery spoiled gradient-echo T1-weighted isotropic (e.g., 1.0× 1.0×1.0 mm$^3$, TE/TR/TI=3.7/8.1/864, flip angle 12 degrees, 256×220×170 FOV, NEX=1, 170 slices, duration: 4:11), a 3D fluid attenuated inversion recovery (FLAIR) (e.g., 1.1× 1.1×1.1 mm$^3$, TE/TR/TI=350/4800/1600, flip angle 90 degrees, 250×250×180 FOV, NEX=1, 163 slices, duration: 5:02) and a 3D T2 sequence acquired in a sagittal plane (e.g., 1.0×1.0×1.0 mm$^3$, TE/TR/TI=229/2500/1600, flip angle 90 degrees, 250×250×180 FOV, NEX=1, 164 slices, duration: 4:33). However, other types of 2D and 3D MRI scanners and other MRI imaging study parameters may be used, such as anisotropic MRI scanners.

In the embodiments shown, image segmentation of the MRI images was performed using segmentation software (e.g., aySegmentation v1.00.004 plug-in of aycan OsiriX® PRO v3.00.008). However, other types and/or methods of image segmentation may be used. During segmentation, focal brain lesions were selected from simultaneously viewed high-resolution T1-weighted, T2-weighted, and FLAIR sequences. All identified focal lesions within the supratentorial region were selected manually and segmented lesions were saved as specified regions of interest (ROI). Intra-observer variability analyses were performed on segmented lesions to ensure accuracy of the obtained data. All selected ROIs were exported into stereolithography (.stl) format and evaluated using 3D software (e.g., MeshLab, Visual Computing Lab—ISTI—CNR, v1.3.3). One or more 3D maximum intensity projection (MIP) images were generated using the 3D software, allowing for 3D spatial visualization of the brain and lesions of the selected ROI. However, other types and/or methods of 3D image creation may be used.

Identified lesions depicted by the 3D images were printed using a MakerBot® Replicator 2× Experimental 3D unit with 1.75 mm acrylonitrile butadiene styrene (ABS) filament with a build platform temperature of 110° F. and an extruder temperature of 230° F. Using fused filament fabrication, a 200 μm layer resolution was achieved with the printed files. Individual lesions were printed at actual size and also enlarged with at least one side measuring at least 10 mm. However, other types of 3D printers and/or other types of 3D printing technologies may be used to create 3D printed molds of the identified lesions. Other degrees of resolution may also be achieved.

Throughout the segmentation process from both MS patients and those with non-specific white matter changes within the brain, lesion characteristics were identified that appeared representative of features associated with MS or non-specific white matter disease from the 3D orthographic image and the corresponding 3D printed lesion representations. These characteristics were separated into primary and secondary characteristics, with primary traits applying to all lesions, and secondary features applying only when present. Exemplary primary and secondary characteristics and definitions may be found in Table 1 below.

TABLE 1

Primary and Secondary Lesion Characteristic Definitions for 3-Dimensional Lesion Scoring

| Primary Characteristics | |
| --- | --- |
| Asymmetric | The lesion does not display an axis of symmetry in any plane of view. |
| Symmetric | The lesion displays relative symmetry from at least one point of view. |
| Complex surface morphology | The lesion displays a complex surface, accented by microirregularities along the surface of the structure. |
| Simple surface morphology | The lesion displays a relatively smooth surface with very few surface. irregularities. |
| Secondary characteristics* | |
| Elongated with nonuniform mass distribution | The lesion is characterized by one axis being significantly longer than the other two, giving it an elongated appearance. It also displays nonuniform mass. distribution throughout its length. |
| Multilobular | The lesion is characterized by having multiple distinct lobules (bumps) that are not surface characteristics, but rather structural features. |
| Protrusion | The lesion is characterized by a distinct elongated tail protruding from the general mass of the lesion. |

TABLE 1-continued

Primary and Secondary Lesion Characteristic Definitions for 3-Dimensional Lesion Scoring

| Sloped Edge | The lesion has a distinct sloped edge involving a single surface. |
| --- | --- |
| Spherocylindrical | The lesion resembles a cylinder with two hemispherical ends. |
| Tapered | The lesion is characterized by a gradual taper in size across the lesion. |
| Wedge shaped | The lesion displays a wedge-like shape, similar to a wedge of an axe. |
| Arched indentation | The lesion has a clearly defined concave groove on the surface. |

*Optional characteritics selected by raters.

As a part of the testing, the characteristics from lesions in 3D printed form were independently rated by three healthcare providers: i) a board certified neurologist and fellowship trained MS specialist with subspecialty interest in neuroimaging, ii) a certified advanced practice provider in MS, and iii) a board certified neuroradiologist. All raters were blinded to the baseline demographic data, clinical diagnosis, whether MS or other etiology, and results from para-clinical data, including MRI features. Raters were also blinded to the scores generated by other evaluators. For each lesion, raters were instructed to score primary characteristics including symmetry (symmetric or asymmetric) and morphology (simple or complex surface morphology). Complex surface morphology may be characterized by a presence of micro-irregularities on the surface of a lesion. An option to select from eight secondary characteristics was also provided to further describe the lesions. These secondary characteristics may include multi-lobular, elongated with irregular mass distribution, protrusion, sloped, wedge-shaped, tapered, arched indentation, and spherocylindrical characteristics, or the like. If an additional characteristic was not appreciated, raters were informed to select 'none'. The final data analysis was performed on consensus scores from the three raters.

Concordance among raters was estimated by the Fleiss extension of the k-statistic. Demographic characteristics were compared between groups using a t-test for normally distributed data, a t-test on log-transformed variables for continuous variables with a skewed distribution (disease duration variables), and by a $\chi2$ test for binary variables. A negative binomial regression model was used to compare the number of lesions with specific traits between groups after adjusting for age and disease duration.

A lesion-level analysis was performed by comparing each lesion characteristic (primary and secondary traits) between patient groups by a mixed binary logistic model including a random intercept to adjust for patient effect, with the studied characteristic as the dependent variable and the clinical diagnosis as the independent variable. A patient-level analysis was completed comparing the percentage of lesions with each characteristic between groups by a logistic model. All analyses were adjusted for age. A $\chi2$ test was used to assess the association between lesion location and lesion type.

To assess for lesion patterns with a set of common characteristics rather than analyzing each characteristic at a time, a latent class analysis (LCA) may be applied, which is an unsupervised statistical method for detecting multiple sets of patterns among subjects with multiple binary characteristics, to identify the optimal number of latent classes (LCs). Models with increasing number of LCs were fitted on the data and the best model was determined according to parsimony criteria and clinical interpretability in combination with three indicators of model fit: Akaike (AIC) and Bayesian information criterion (BIC) and the likelihood ratio statistic (G2). Lower AIC, BIC, and G2 values were preferred. The posterior membership probabilities were estimated directly from the model parameters and used to assign lesions to the class for which the posterior probability was highest. A P-value of <0.05 was considered significant.

A total of 30 patients (19 with a confirmed diagnosis of MS [11 female; median age=33.6 years, range: 26.9-54.5]), median disease duration=2.2 years [0.4-19.4]), 11 with verified NSWM disease without MS (11 female; median age=55.0 years, range: 27.9-66.2), were enrolled in this study. Of the patients within the NSWM group, 4 had a history of migraine headaches. Four patients declined participation and were not enrolled due to the required time commitment (n=2), travel costs to the imaging center (n=1), and recent inner ear surgery (n=1). The baseline demographic and clinical features of the study cohort are summarized in Table 2 below.

TABLE 2

Demographic and Clinical Characteristic Data of the Study Cohort by Diagnosis

| Diagnosis: Multiple Sclerosis (n = 19) | |
| --- | --- |
| Age at first symptom, median years (range) | 30.2 (19.5-53.1) |
| Age at 3D MRI* | 33.6 (26.9-55.6) |
| Sex$^£$ | F: 11 (58%); M: 8 (42 |
| Ethnicity | Non-Hispanic: 17 (89%); Hispanic 2 (11%) |
| Disease duration | 2.2 (.37-19.44) |
| Diagnosis: Nonspecific White Matter Disease (n = 11) | |
| Age at first abnormal MRI, median, years range) | 42.4 (27.5-52.9) |
| Age at 3D MRI* | 55.0 (27.9-66.2) |
| Sex$^£$ | F: 11 (100%) |
| Ethnicity | Non-Hispanic: 9 (82%); Hispanic: 2 (18%) |
| Disease duration | 4 (36.4%) |

*Statistical difference between groups (P < .001).
$^£$Statistical difference groups (P = .003).

A total of 1,013 focal brain lesions were isolated and stereolithography files and 3D prints of the selected regions of interest were created. Twelve lesions were removed from the analysis due to reduced 3D print quality, resulting in 1,001 lesions available for analysis. Of the 1,001 lesions, 710 were isolated from MS patients and 291 from patients with non-specific white matter disease. Concordance in lesion characteristic classification was moderate-high among the three-blinded raters for both primary and secondary lesion characteristics with k-values ranging from 0.48 (asymmetric) to 0.83 (protrusion).

The results from the primary classification of all lesions revealed that 66.3% were asymmetric in 3D shape and 54.8% were associated with complex surface characteristics. A higher percentage of asymmetric lesions was appreciated in those subjects with MS when compared to the non-specific white matter group (75.9% versus 43%; OR: 4.39 [2.37-8.12]; p<0.001). In addition, MS lesions were more highly associated with complex surface morphologies (65.9% versus 27.8%; OR: 2.3 [1.74-3.05]; p<0.001). These results were unchanged when adjusting for age. A significant association between the two primary characteristics of lesion asymmetry and complex surface morphology was also observed (p<0.001).

The global number of lesions classified with secondary characteristics and the observed frequencies according to disease group is reported in Table 3 below. Results from the mixed binary logistic model, accounting for the autocorrelation of measures within the same patient, revealed significant differences between groups when lesions were described as being multilobular (11.0% vs. 0.3%, P<0.001) or elongated (12.8% vs. 2.4%, P<0.001).

TABLE 3

Summary of the Frequency of Primary and Secondary Characteristics of All MRI Lesions Studied

| Diagnosis: | Multiple Sclerosis | Nonspecific White Matter |
| --- | --- | --- |
| Primary Lesion Characteristics | | |
| Asymmetric shape*, n (% within diagnosis) | 539 (75.9%) | 125 (43.0%) |
| Complex surface morphology | 468 (65.9%) | 81 (27.8%) |
| Secondary Lesion Characteristics | | |
| Multilobular*, n (% within diagnosis) | 56 (7.9%) | 1 (.3%) |
| Elongated* | 91 (12.8%) | 7 (2.4%) |
| Protrusion$^£$ | 20 (2.8%) | 0 (.0%) |
| Sloped$^£$ | 12 (1.7%) | 0 (.0%) |
| Spherocylindrical | 18 (2.5%) | 18 (6.2%) |
| Wedge | 4 (.6%) | 2 (.7%) |
| Tapered | 18 (2.5%) | 7 (2.4%) |
| Arched indentation | 8 (1.1%) | 10 (3.4%) |

*Statistical difference between groups (P < .001).
$^£$Lesion characteristic only observed in MS patients.

Results from a mixed binary logistic model, accounting for the autocorrelation of measures within the same patient, revealed significant differences between groups when lesions were described as being multi-lobular (7.9% versus 0.3%, p<0.001), elongated (12.8% versus 2.4%, p<0.001), and associated with a protrusion (3.6% versus 0%, p=0.02). The average volume (0.25 $cm^3$ versus 0.06 $cm^3$, p<0.001) and length of the longest side was observed to be higher in MS than in non-specific white matter disease patients. Statistically significant differences were not observed for lesions described with the following secondary characteristics: wedge, tapered, sloped, arched indentation, and spherocylindrical. However, those lesions described as containing a sloped trait were only observed in subjects with MS (12 (100%) versus 0%). In addition, spherocylindrical lesions were observed at a higher frequency in patients with non-specific white matter disease (6.2% versus 2.5%, trend towards significance).

Significant differences were observed in the spatial distribution of asymmetric (P<0.001), complex surface characteristics (P<0.001), elongated (P=0.001), multilobular (P<0.001) and lesions with protrusions (P=0.02) in the juxtacortical, subcortical, deep white matter, or periventricular areas. These lesion types were observed in all spatial regions but at higher frequencies in nonsubcortical regions.

The LCA, applied to identify typical patterns of lesions rather than analyzing each characteristic individually, recognized three optimum lesion classification classes. Class 1 included 456 lesions (45.5%); class 2 included 449 lesions (44.9%); and class 3 with 96 lesions (9.6%). The lesion characteristics in each class are reported in Table 4 below. Class 2 and class 3 lesions were primarily both asymmetric and complex, and class 3 was characterized by these two characteristics along with being elongated. Class 1 was characterized by being symmetric and simple. Moreover, all multilobular lesions were found in class 2, while the majority of lesions that were wedge-shaped (83%) and spherocylindrical (97%) were observed in class 1. The average size of lesions was larger in the higher classes, with class 3 being larger than class 2, and class 2 being larger than class 1 (Table 4).

TABLE 4

Data from the Latent Class Analysis Demonstrating Lesion Characteristics within Each Class Along with Lesion Size and Volumes

| Lesion Characteristic | Class 1<br>n = 456 | Class 2<br>n = 449 | Class 3<br>n = 96 | Total |
|---|---|---|---|---|
| Asymmetric shape, n (% among classes) | 119 (18%) | 449 (68%) | 96 (14%) | 664 |
| Complex surface morphology | 11 (2%) | 449 (82%) | 89 (16%) | 549 |
| Multilobular | 0 (0%) | 57 (100%) | 0 (0%) | 57 |
| Elongated | 2 (2%) | 0 (0%) | 96 (98%) | 98 |
| Protrusion | 0 (0%) | 20 (100%) | 0 (0%) | 20 |
| Sloped | 3 (25%) | 9 (75%) | 0 (0%) | 12 |
| Spherocylinderical | 35 (97%) | 1 (3%) | 0 (0%) | 36 |
| Wedge | 5 (83%) | 1 (17%) | 0 (0%) | 6 |
| Tapered | 18 (64%) | 10 (36%) | 0 (0%) | 28 |
| Arched indentation | 13 (72%) | 5 (28%) | 0 (0%) | 18 |
| Size and Volume | | | | |
| Longest side, mm, size (standard deviation) | 5.1 (2.5) | 10.1 (5.7) | 14.6 (7.9) | |
| Total X, Y, Z, mm | 11.6 (5.1) | 22.8 (11.6) | 25.6 (12.4) | |
| Volume, mm$^3$ | .04 (.1) | .2 (.4) | .2 (.3) | |
| Surface area, mm$^2$ | .7 (2.3) | 2.0 (2.3) | 2.3 (2.1) | |

A patient-level analysis was performed to correlate lesion patterns to disease state. The percentage of lesions with each characteristic was calculated for all patients, in addition to the percentage of lesions in each class resulting from the LCA analysis. The percentage of lesions was significantly different between patients with MS and patients with NSWM disease for lesions that were asymmetric (P=0.001), had a complex surface morphology (P=0.001), were elongated (P=0.003), and multilobular (P<0.001). The average volume (0.25 cm3[standard deviation [SD]0.34] vs. 0.06 cm3 [0.081], P<0.001) and length of the longest side (9.47 mm [6.22] vs. 5.21 mm [2.84], P<0.001) was also observed to be higher in MS than in NSWM disease patients. When all studied patients were classified according to their lesion patterns from LCA, 14 patients were identified with class 1 lesion traits and 16 patients with class 2 features. Among the 19 MS patients, 14 had class 2 lesions (5 class 1 cases) compared to the 11 NSWM disease patients in which only 2 demonstrated a class 2 pattern (sensitivity 74%, specificity 82%, and accuracy 77%).

Results confirmed that MS lesions may be more amorphous with complex surface morphologies as opposed to lesions that exhibit a degree of symmetry such as an ovoid morphology. Lesions typical for MS were identified to be asymmetric with complex surface morphologies that were more multilobular, elongated with non-uniform mass distributions, and contained protrusions. These traits were also identified at higher frequencies within the deep white matter and periventricular regions contributing additional information beyond spatial dissemination. The clustering of lesion characteristics also appeared to support shape and surface differences between groups with a high degree of accuracy. These findings were supported by both an analysis involving individual lesion characteristics in relation to disease state and at the patient level while adjusting for age. Lesions with a definable protrusion or slope were only identified in patients with MS and the lack of statistical significance appeared to be related to the low observed frequency within patients and total lesions studied. Even through the simultaneous evaluation of axial, sagittal, and coronal views on MRI, a limited appreciation of the spatial geometry of T2-hyperintensities may exist, emphasizing the value and need of a 3D approach to lesion assessment.

Example experimental results are depicted in FIGS. 6-9. In the embodiment shown in FIG. 6, results 600 may include one or more 2D MRI images 602, one or more 3D MRI images 604, one or more 3D brain lesion images 606, and one or more 3D physical brain lesion representations 608. In the embodiment shown, one or more 2D MRI images 602 are axial MRI FLAIR images of the brain, one or more 3D MRI images 604 are MIP images, one or more 3D brain lesion images 606 are orthographic images, and one or more 3D physical brain lesion representations 608 are 3D printed regions of interest from four unique patients. In the embodiment shown, images A-D exhibit asymmetric primary lesion characteristics, images E-H exhibit symmetric primary lesion characteristics, images I-L exhibit complex surface morphology primary lesion characteristics, and images M-P exhibit simple surface morphology primary lesion characteristics.

Figure 7:
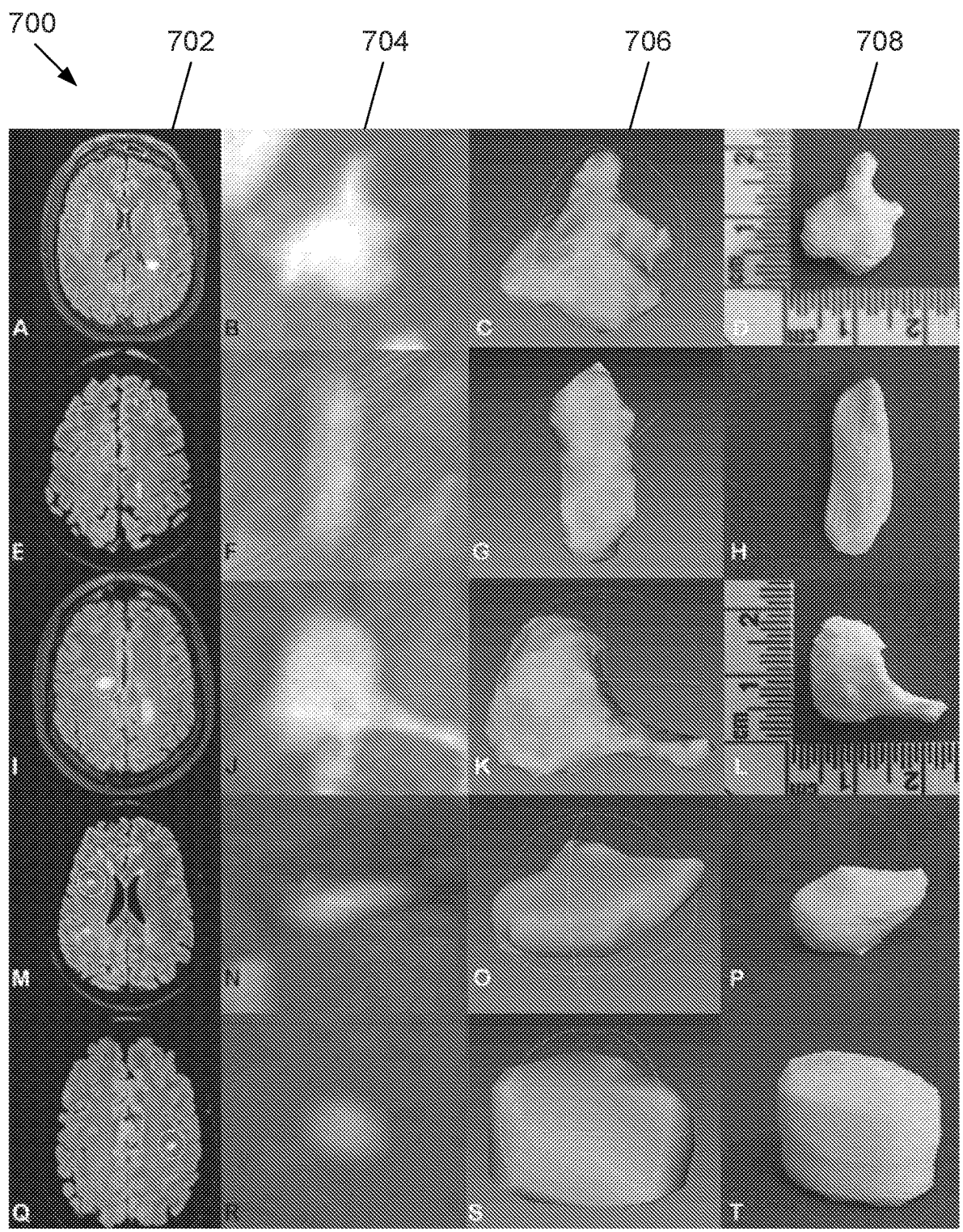
FIG. 7 depicts exemplary experimental results from an implementation of the systems and methods described by another embodiment of the disclosure.

In the embodiment shown in FIG. 7, results 700 may include one or more 2D MRI images 702, one or more 3D MRI images 704, one or more 3D brain lesion images 706, and one or more 3D physical brain lesion representations 708. In the embodiment shown, one or more 2D MRI images 702 are axial MM FLAIR images of the brain, one or more 3D MRI images 704 are MIP images, one or more 3D brain lesion images 706 are orthographic images, and one or more 3D physical brain lesion representations 708 are 3D printed regions of interest from five unique patients. In the embodiment shown, images A-D exhibit multi-lobular secondary lesion characteristics, images E-H exhibit elongated secondary lesion characteristics with a non-uniform distribution of mass, images I-L exhibit protrusion secondary lesion characteristics, images M-P exhibit sloped edge secondary lesion characteristics, and images Q-T exhibit spherocylindrical secondary lesion characteristics. In the embodiment shown, images A-P depict secondary lesion characteristics associated with MS etiologies and images Q-T depict secondary lesion characteristics associated with non-specific white matter etiologies.

Figure 8:
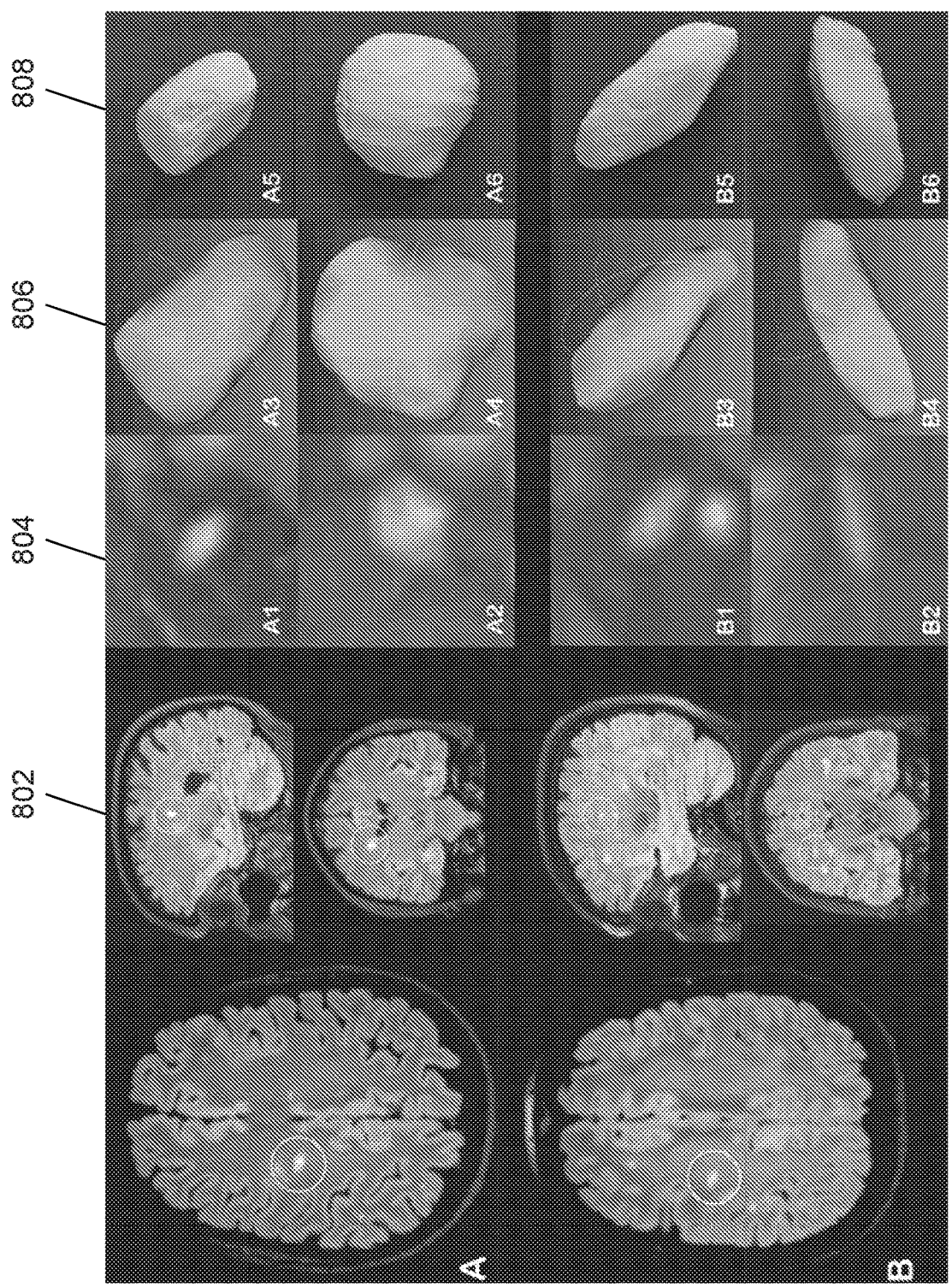
FIG. 8 depicts exemplary experimental results from an implementation of the systems and methods described by another embodiment of the disclosure.

In the embodiment shown in FIG. 8, results 800 may include one or more 2D MRI images 802, one or more 3D MRI images 804, one or more 3D brain lesion images 806, and one or more 3D physical brain lesion representations 808. In the embodiment shown, one or more 2D MRI images 802 are axial MRI FLAIR images of the brain, one or more 3D MRI images 804 are MIP images, one or more 3D brain lesion images 806 are orthographic images, and one or more 3D physical brain lesion representations 808 are 3D printed regions of interest from two unique patients. In the embodiment shown, the images in group A correspond to a patient with MS and the images in group B correspond to a patient with a non-specific white matter disease or condition. It can be seen that the lesions shown in the one or more 2D MRI images 802 may have a similar appearance. This illustrates the limitations of 2D MRI images when attempting to determine brain lesion etiologies. It can be seen that the one or more 3D MRI images 804 and one or more 3D brain lesion images 806 may provide a more accurate depiction of primary and secondary lesion characteristics. The one or more 3D physical brain lesion representations 808 may provide even more detail regarding the primary and secondary lesion characteristics.

Figure 9:
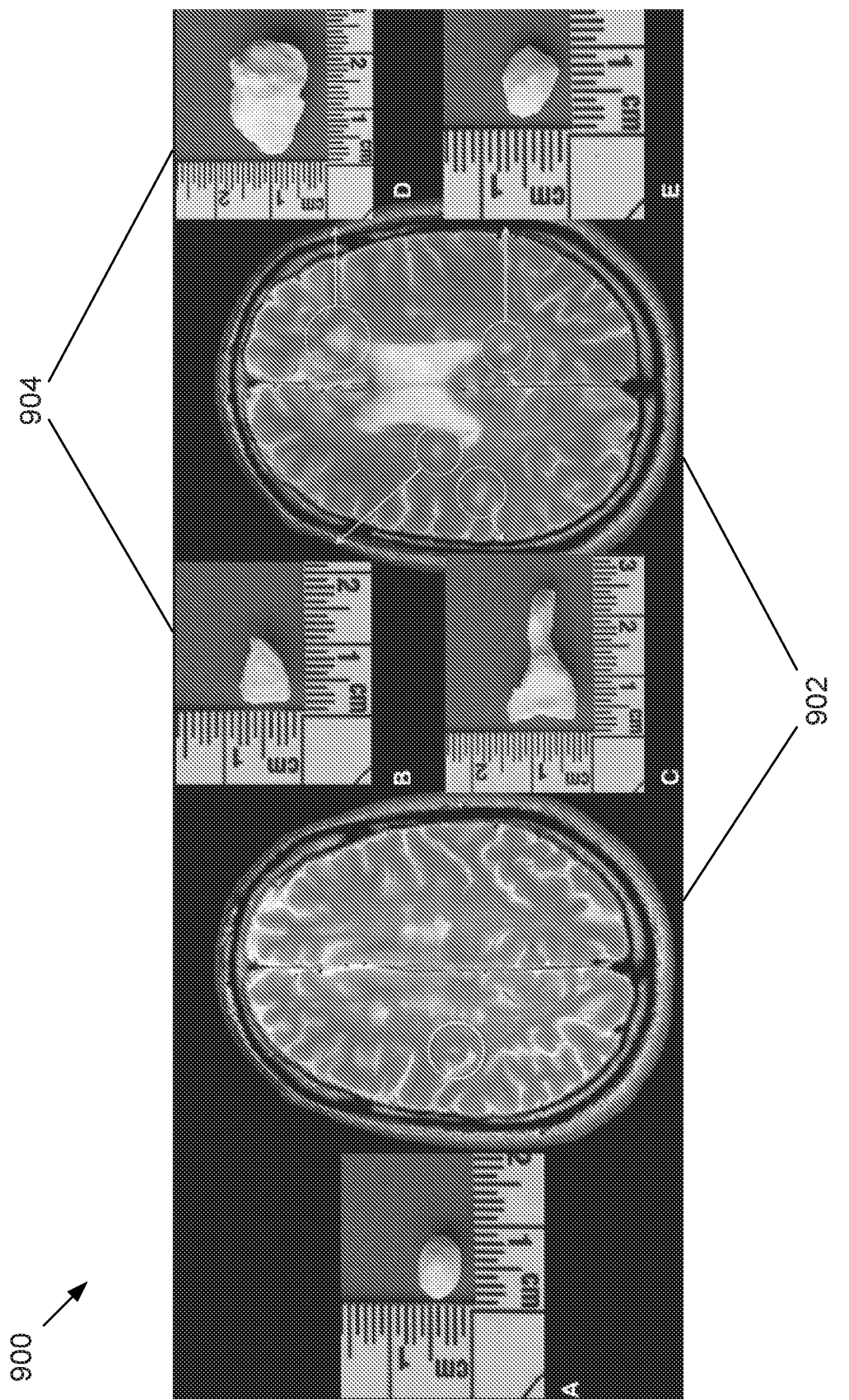
FIG. 9 depicts exemplary experimental results from an implementation of the systems and methods described by another embodiment of the disclosure.

In the embodiment shown in FIG. 9, results 900 may include one or more 2D MRI images 902 and one or more 3D physical brain lesion representations 904. In the embodiment shown, one or more 2D MRI images 902 are axial MRI FLAIR images of the brain and one or more 3D physical brain lesion representations 904 are 3D printed regions of interest from a patient having MS. In the embodiment shown, image A exhibits a spherocylindrical secondary lesion characteristic, image B exhibits a wedge-shaped secondary lesion characteristics, image C exhibits protrusion secondary lesion characteristics, and image D exhibits multi-lobular secondary lesion characteristics. Additionally, images A and B exhibit simple surface morphology primary lesion characteristics and images C-E exhibit complex surface morphology primary lesion characteristics.

As shown in the embodiments of FIGS. 6-9, MS lesions may be more asymmetric and elongated, contain complex surface morphologies, have higher surface area to volume ratios, and may be multi-lobular, sloped, and associated with protrusions. Lesions associated with non-specific white matter conditions such as migraines, small vessel disease, and cryptogenic white matter causes may be more symmetric, contain simple surface morphologies, have lower surface area to volume ratios, and may be spherocylindrical and/or tapered/wedge-shaped. Therefore, by associating these primary and secondary lesion characteristics with corresponding etiologies, the disclosed systems and methods may enable a more accurate and efficient determination of brain lesion etiologies.

These results may assist in adjusting clinical expectations related to a treatment goal of no evidence of disease activity (NEDA) in MS, a therapeutic goal based on the absence of clinical relapses, radiological evolution, and reductions in physical function. An admixture of non-specific foci and in situ demyelination would be expected given the range of ages for MS subjects studied here and the higher prevalence of small vessel disease appreciated on MRI with advancing age, suggesting that the magnitude of the observed differences between groups may be greater. Lesions containing a spherocylindrical pattern were identified at a higher frequency in the non-specific white matter group and were observed to be a highly distinct and consistent 3D trait. As shown in FIG. 9, the identification of spherocylindrical lesions and associated simple surface characteristics within subjects with MS supported the notion of the coexistence of both MS and non-MS MRI lesion phenotypes within a single patient. This data may be of value to established MS patients with radiological evolution, in the absence of contrast enhancement and involvement of highly specific areas for MS. This treatment may provide potential clarity as to the origin of newly found lesions and may prevent an unnecessary change in disease modifying therapy based on NEDA. The data suggests that the development of new T2-foci in MS patients, even when established size thresholds of >3 $mm^2$ are applied, may not be related to inflammatory autoimmune disease.

The observed 3D characteristics between disease states may be related to the biology of lesion development. The relative symmetry observed for white matter lesions isolated from non-MS subjects having less dynamic surface characteristics may be the result of the pathogenesis of such findings, including vascular ectasia, acute or chronic ischemic insults or dilation of perivascular spaces associated with medullary arteries, or atrophic perivascular demyelination caused by a chronic nutritive deficiency that are distinct from ischemic necrosis. Histopathological data from lesions originating from non-MS patients has also been shown to indicate the presence of a central vessel, with features consistent with internal thickening and narrowing of the lumen. Therefore, an arteriosclerotic process may also be plausible. Contemporary histopathological data of demyelinating white matter lesions suggest a great degree of heterogeneity, likely as a result of the interplay between the active and innate immune response. In multiple sclerosis, the immune response is an active biological process, with an inherently aberrant nature. This stochastic process is a likely cause of the diverse, amorphous characteristics observed. While the active immune system is highly specific at a microscopic level, the resulting white matter insult presents a more erratic topography upon macroscopic view. Proposed secondary characteristics are believed to arise from interactions with micro-anatomical boundaries, and may also be the result of the natural evolution of a demyelinating plaque over time.

It may be appreciated that the disclosed embodiments may also be applied to detect and create 3D representations of other biological masses, bodies, or systems within the body. For example, the disclosed embodiments may receive MRI images showing brain or other tumors and/or vascular malformations (e.g., aneurysms). Similar to the above described processes for brain lesions, 3D images of tumors and vascular malformations may be constructed from received 2D images and used to create physical 3D representations of the tumors and vascular malformations. By imaging and creating 3D images and representations of various biological elements, these images and representations may be analyzed over time to determine etiology, a natural history of disease progression, and/or effects of treatment regimens.

In some embodiments, the observed 3D characteristics between disease states may be related to the biology of lesion development. The relative symmetry observed for white matter lesions isolated from non-MS subjects and less dynamic surface characteristics may be the result of the pathogenesis of such findings including vascular ectasia, acute or chronic ischemic insults, dilation of perivascular spaces associated with medullary arteries, or atrophic perivascular demyelination caused by a chronic nutritive deficiency that is distinct from ischemic necrosis. Histopathological data from lesions originating from non-MS patients have also been shown to indicate the presence of a "central vessel" with features consistent with internal thickening and narrowing of the lumen. Contemporary histopathological data of demyelinating white matter lesions suggest a great degree of heterogeneity, likely as a result of the interplay between the active and innate immune response. In MS, the immune response is an active biological process with an inherently aberrant nature. This stochastic process is a likely cause of the diverse, amorphous characteristics observed in shape and texture.

Figure 10:
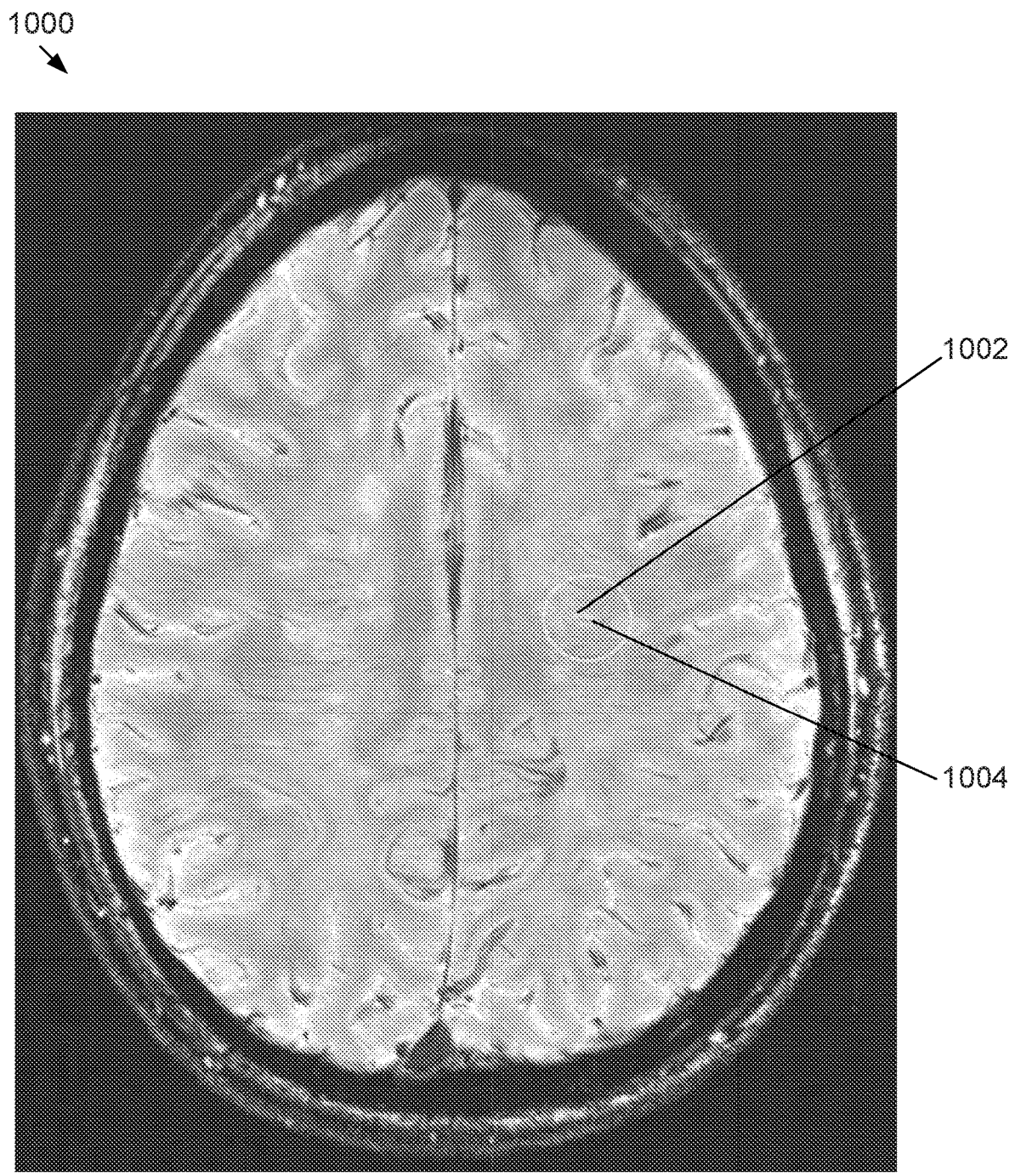
FIG. 10 depicts an exemplary 2D MRI image that may be received according to an embodiment of the disclosure.

FIG. 10 depicts an exemplary 2D MRI image 1000 that may be received according to an embodiment of the disclosure. In some embodiments, one or more 3D MRI images may be used. In the embodiment shown, a brain lesion 1002 is shown to contain one or more blood vessels 1004. These blood vessels or venules may comprise vasculature that may be present within and/or traverse the lesion. Certain histopathological studies at autopsy have shown that a large number of MS lesions are centered around one or more veins or "central vessels." Injuries related to MS may result from inflammatory cells that are able to exit the blood vessels within the lesion, causing damage to the surrounding myelin and nerve fibers of the brain. The presence, absence, and characteristics/structures of these blood vessels may constitute a "central vessel sign" that may assist in a determination of the etiology of the brain lesion. In other words, the observation of this "central vessel sign" may increase lesion specificity for MS. However, a 2D view in multiple planes of view (i.e. axial, sagittal, and coronal) such as that depicted in FIG. 10, cannot provide an adequate assessment of the location of the blood vessels nor the vessel characteristics (i.e., if they are tortuous, etc.). This limitation is similar to that shown in the embodiments depicted in FIG. 8. The embodiments described herein can also receive one or more 2D MRI images such as image 1000 and/or one or more 3D MRI images and create accurate 3D depictions of vasculature that may be present within a brain lesion. Any vasculature present within the lesion can be represented in a 3D physical brain lesion representation printed or otherwise created from the 3D depictions of the lesion. In this way, beyond external characteristics of shape and surface texture of brain lesions, the disclosed embodiments may assist with learning more about the vessel characteristics within lesions by studying anatomy within the selected 3D regions of interest. It may also enable a determination of the extent of damage inside a particular brain lesion in addition to the shape and surface characteristics of the outside of the lesion.

It may be appreciated that the functions described above may be performed by multiple types of software applications, such as web applications or mobile device applications. If implemented in firmware and/or software, the functions described above may be stored as one or more instructions or code on a non-transitory computer-readable medium. Examples include non-transitory computer-readable media encoded with a data structure and non-transitory computer-readable media encoded with a computer program. Non-transitory computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom VLSI circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or very large scale integrated (VLSI) circuits. In fact, persons of ordinary skill in the art may utilize any number of suitable structures capable of executing logical operations according to the described embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A system for creating 3-dimensional (3D) representations of brain lesions, the system comprising:
    a computer system comprising at least one processor configured to:
        receive one or more 3D images of a brain;
        enable an identification of one or more brain lesions in the one or more 3D images of the brain;
        enable a segmentation of the one or more 3D images, the segmentation enabling an isolation of the one or more brain lesions;
        enable a creation of one or more 3D brain lesion images based on the segmentation, the one or more 3D brain lesion images comprising one or more lesion characteristics;
        enable a comparison of the one or more lesion characteristics of the one or more 3D brain lesion images with one or more predetermined lesion characteristics;
        enable a determination of a type of the one or more brain lesions based on a match between the one or more lesion characteristics of the one or more 3D brain lesion images and the one or more predetermined lesion characteristics; and enable the sending of 3D representation data corresponding to the one or more 3D brain lesion images, the 3D representation data configured to enable a creation of one or more physical 3D representations of the one or more brain lesions;

where the one or more lesion characteristics comprise one or more of geometric characteristics and surface characteristics, and the geometric characteristics comprise a symmetry characteristic, a surface morphology characteristic, a lobular shape characteristic, a protrusion characteristic, a slope characteristic, a tapered shape characteristic, and a spherocylindrical shape characteristic.

2. The system of claim 1, the computer system further configured to:

receive one or more 2D images of a brain; and enable a creation of one or more 3D images of the brain based on the one or more 2D images of the brain.

3. The system of claim 1, where the one or more 3D images comprise one or more maximum intensity projection (MIP) images, the MIP images configured to enable 3D spatial visualization of the brain.

4. The system of claim 1, where the one or more 3D brain lesion images comprise one or more orthographic projections in stereolithographic format.

5. The system of claim 1, where the one or more physical 3D representations comprise fused filament 3D printed models.

6. The system of claim 1, where the one or more 3D images of the brain comprise one or more isotropic magnetic resonance imaging (MRI) images.

7. The system of claim 1, where the one or more predetermined lesion characteristics correspond to one or more lesion characteristics associated with one or more disease etiologies.

8. The system of claim 7, where the one or more disease etiologies comprise one or more of multiple sclerosis (MS) and non-specific categories.

9. The system of claim 8, where the non-specific categories comprise aging, migraine headache, small vessel disease, and cryptogenic white matter.

10. The system of claim 1, where the one or more 3D brain lesion images comprise one or more lesion vasculature characteristics.

11. A system for creating 3-dimensional (3D) representations of brain lesions, the system comprising:

a computer system comprising at least one processor configured to:

receive one or more 3D images of a brain;

enable an identification of one or more brain lesions in the one or more 3D images of the brain;

enable a segmentation of the one or more 3D images, the segmentation enabling an isolation of the one or more brain lesions;

enable a creation of one or more 3D brain lesion images based on the segmentation, the one or more 3D brain lesion images comprising one or more lesion characteristics;

enable a comparison of the one or more lesion characteristics of the one or more 3D brain lesion images with one or more predetermined lesion characteristics;

enable a determination of a type of the one or more brain lesions based on a match between the one or more lesion characteristics of the one or more 3D brain lesion images and the one or more predetermined lesion characteristics; and enable the sending of 3D representation data corresponding to the one or more 3D brain lesion images, the 3D representation data configured to enable a creation of one or more physical 3D representations of the one or more brain lesions;

where the one or more lesion characteristics comprise one or more of geometric characteristics and surface characteristics, and the surface characteristics comprise a surface topography characteristic, a surface irregularity characteristic, a surface area to volume ratio characteristic, and a distribution of mass characteristic.

12. A method of creating 3-dimensional (3D) representations of brain lesions, the method comprising:

receiving, by a computer system comprising at least one processor, one or more 3D images of a brain;

enabling, by the computer system, an identification of one or more brain lesions in the one or more 3D images of the brain;

enabling, by the computer system, a segmentation of the one or more 3D images, the segmentation enabling an isolation of the one or more brain lesions;

enabling, by the computer system, a creation of one or more 3D brain lesion images based on the segmentation, the one or more 3D brain lesion images comprising one or more lesion characteristics;

enabling, by the computer system, a comparison of the one or more lesion characteristics of the one or more 3D brain lesion images with one or more predetermined lesion characteristics;

enabling, by the computer system, a determination of a type of the one or more brain lesions based on a match between the one or more lesion characteristics of the one or more 3D brain lesion images and the one or more predetermined lesion characteristics; and enabling, by the computer system, the sending of 3D representation data corresponding to the one or more 3D brain lesion images, the 3D representation data configured to enable a creation of one or more physical 3D representations of the one or more brain lesions;

where the one or more lesion characteristics comprise one or more of geometric characteristics and surface characteristics, and the geometric characteristics comprise a symmetry characteristic, a surface morphology characteristic, a lobular shape characteristic, a protrusion characteristic, a slope characteristic, a tapered shape characteristic, and a spherocylindrical shape characteristic.

13. The method of claim 12, further comprising:

receiving, by the computer system, one or more 2D images of a brain; and enabling, by the computer system, a creation of one or more 3D images of the brain based on the one or more 2D images of the brain.

14. The method of claim 12, where the one or more segmented images comprise one or more maximum intensity projection (MIP) images, the MIP images configured to enable 3D spatial visualization of the brain.

15. The method of claim 12, where the one or more 3D brain lesion images comprise one or more orthographic projections in stereolithographic format.

16. The method of claim 12, where the one or more physical 3D representations comprise fused filament 3D printed models.

17. The method of claim 12, where the one or more 3D images of the brain comprise one or more isotropic magnetic resonance imaging (MRI) images.

18. The method of claim 12, where the one or more predetermined lesion characteristics correspond to one or more brain lesion characteristics associated with one or more disease etiologies.

19. The method of claim 18, where the one or more disease etiologies comprise one or more of multiple sclerosis (MS) and non-specific categories.

20. The method of claim 19, where the non-specific categories comprise aging, migraine headache, small vessel disease, and cryptogenic white matter.

21. The system of claim 12, where the one or more 3D brain lesion images comprise one or more lesion vasculature characteristics.

22. A method of creating 3-dimensional (3D) representations of brain lesions, the method comprising:

receiving, by a computer system comprising at least one processor, one or more 3D images of a brain;

enabling, by the computer system, an identification of one or more brain lesions in the one or more 3D images of the brain;

enabling, by the computer system, a segmentation of the one or more 3D images, the segmentation enabling an isolation of the one or more brain lesions;

enabling, by the computer system, a creation of one or more 3D brain lesion images based on the segmentation, the one or more 3D brain lesion images comprising one or more lesion characteristics;

enabling, by the computer system, a comparison of the one or more lesion characteristics of the one or more 3D brain lesion images with one or more predetermined lesion characteristics;

enabling, by the computer system, a determination of a type of the one or more brain lesions based on a match between the one or more lesion characteristics of the one or more 3D brain lesion images and the one or more predetermined lesion characteristics; and enabling, by the computer system, the sending of 3D representation data corresponding to the one or more 3D brain lesion images, the 3D representation data configured to enable a creation of one or more physical 3D representations of the one or more brain lesions;

where the one or more lesion characteristics comprise one or more of geometric characteristics and surface characteristics, and the surface characteristics comprise a surface topography characteristic, a surface irregularity characteristic, a surface area to volume ratio characteristic, and a distribution of mass characteristic.

* * * * *